(12) United States Patent
Kotani et al.

(10) Patent No.: US 7,767,881 B2
(45) Date of Patent: Aug. 3, 2010

(54) UTILIZATION OF HISTAMINE RECEPTOR H3 GENE PARTICIPATING IN BODY WEIGHT OR FOOD INTAKE CONTROL

(75) Inventors: Hidehito Kotani, Ibaraki (JP); Kazuhiko Takahashi, Ibaraki (JP); Hiroaki Suwa, Ibaraki (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 359 days.

(21) Appl. No.: 10/482,464

(22) PCT Filed: Jun. 28, 2002

(86) PCT No.: PCT/JP02/06580

§ 371 (c)(1), (2), (4) Date: Jul. 27, 2004

(87) PCT Pub. No.: WO03/004637

PCT Pub. Date: Jan. 16, 2003

(65) Prior Publication Data

US 2004/0259778 A1 Dec. 23, 2004

(30) Foreign Application Priority Data

Jul. 2, 2001 (JP) .............................. 2001-201413

(51) Int. Cl.
*A01K 67/027* (2006.01)
*A01K 67/00* (2006.01)
*A01K 67/033* (2006.01)
*G01N 33/00* (2006.01)
*C12N 5/00* (2006.01)
*C12N 5/02* (2006.01)
*C12N 5/07* (2006.01)
*C12N 5/10* (2006.01)

(52) U.S. Cl. .................... 800/18; 435/325; 435/354; 800/8; 800/3

(58) Field of Classification Search .............. 800/3, 800/8, 21, 18; 435/325
See application file for complete search history.

(56) References Cited

U.S. PATENT DOCUMENTS

| 5,486,526 | A | 1/1996 | Durant et al. |
| 5,882,893 | A | 3/1999 | Goodearl ............... 435/69.1 |
| 6,136,559 | A | 10/2000 | Lovenberg et al. |

FOREIGN PATENT DOCUMENTS

| AU | 200038576 | 11/2000 |
| WO | WO 95/11894 | 5/1999 |
| WO | WO 99/28470 | 6/1999 |
| WO | WO 00/20011 | 4/2000 |
| WO | WO 00/64884 | 11/2000 |
| WO | WO 03/039245 | * 5/2003 |

OTHER PUBLICATIONS

Coge et al. (2001) Biochem J. 355:279-288.*
Murray (1999) Theriogenology 51:149-159.*
Lariviere et al. (2001) J. Pharm. And Exp. Therap. 297:467:473.*
Thomson et al. (1998) Science, vol. 282, p. 1145-7.*
Campbell et al. (1997) Theriogenology, vol. 47 (1), p. 65.*
Houdebine, L.-M., (2002) Journal of Biotechnology, vol. 98, p. 145-160.*
Clark et al. (2000) Gene targeting in livestock: a preview. Transgenic Research 9:263-275.*
(Denning et al. (2001) Gene targeting in Primary Fetal Fibroblasts from Sheep and Pig. Cloning and Stem Cells. 3:221-231.*
Pennisi and Vogel (2000) Clones: A hard act to follow. Science. 288:1722-1727.*
Mitalipov et al. (2002) Rhesus Monkey Embryos Produced by Nuclear Transfer From Embryonic Blastomeres or Somatic Cells. 66:1367-1373.*
Moreadith et al. (J. Mol. Med., 1997), 75:208-216.*
Seamark (Reproductive Fertility and Development, 1994), 6:653-657.*
Mullins et al. (Journal of Clinical Investigation, 1996) 98:S37-S40.*
Gerlai, TINS, 19:177-181,1996.*
Hara, J. Neuroscience Letters, 380:239-242, 2005.*
Yates SL et al., "Effects of a novel histamine $H_3$ receptor antagonist, GT-2394, on food intake and weight gain in Sprague-Dawley rats", Society for Neuroscience Abstracts, vol. 26(1-2) p. Abstract No. 10210 (2000).
Itoh, E. et al., "Thiopermide, a histamine $H_3$ receptor antagonist, powerfully suppresses peptide YY-induced food intake in rats", Biological Psychiatry, vol. 45 (4), pp. 475-481 (1999).
Nakamura T. et al., "Molecular Cloning and Characterization of a New Human Histamine Receptor", Biochemical and Biophysical Research Communications, vol. 279(2), pp. 615-620 (2000).
Ookuma K. et al., "Neuronal histamine in the hypothalamus suppress food intake in rats", Brain Research, vol. 628, pp. 235-242 (1993).
Lovenberg TW et al., "Cloning and Functional Expression of the Human Histamine $H_3$ Receptor", Molecular Pharmacology, vol. 55, pp. 1101-1107 (1999).
Lovenberg et al., "Cloning of Rat Histamine $H_3$ Receptor Reveals Distinct Species Pharmacological Profiles", The Journal of Pharmacology and Experimental Therapeutics, vol. 293 (3), pp. 771-778 (2000).

(Continued)

*Primary Examiner*—Valarie Bertoglio
(74) *Attorney, Agent, or Firm*—Richard C. Billups; John C. Todaro

(57) ABSTRACT

To clarify histamine receptor H3 protein function in vivo, the present inventors constructed a nonhuman higher animal in which the expression of a histamine receptor H3 gene was artificially inhibited. As a result, the present inventors found that this nonhuman higher animal showed increased body weight, food intake, blood insulin level, or blood leptin level compared with a control. Thus, the present inventors found that abnormalities in the histamine receptor H3 protein relate to diseases characterized by changes in body weight or food intake, and this has made it possible to screen drugs for treatment or prevention of these diseases, and to examine these diseases.

13 Claims, 5 Drawing Sheets

OTHER PUBLICATIONS

Tardivel-Lacombe J. et al., "Cloning and cerebral expression of the guinea pig histamine $H_3$ receptor: evidence for two isoforms", Molecular Neuroscience, vol. 11(4), pp. 755-759 (2000).

Marsh D. et al., "Role of the Y5 neuropeptide Y receptor in feeding and obesity", Nature Medicine, vol. 4(6), pp. 718-721 (1998).

Pedrazzini T. et al., "Cardiovascular response, feeding behavior and locomotor activity in mice lacking the NPY Y1 receptor", Nature Medicine, vol. 4(6), pp. 722-726 (1998).

Lin J.S. et al., "Evidence for Histaminergic Arousal Mechanisms in the Hypothalamus of Cat", Neuropharmacology, vol. 27(2), pp. 111-122 (1998).

Schwartz J. et al., "The Third Histamine Receptor", Histaminergic Neurons: Morphology and Function, pp. 85-104 (1991).

Mochizuki T. et al., "In vivo release of neuronal histamine in the hypothalamus of rats measured by microdialysis", Naunyn-Schmiedeberg's Archives of Pharmacology, vol. 343, pp. 190-195 (1991).

Onodera K. et al., "Neuropharmacology of the Histaminergic Neuron System in the Brain and its Relationship with Behavorial Disorders", Progress in Neurobiology, vol. 42, pp. 685-702 (1994).

Mansfield L., "The role of antihistamine therapy in vascular headaches", J. Allergy Clin. Immunol, vol. 86, pp. 673-676 (1990).

Yokoyama H. et al., "Effect of thioperamide, a histamine $H_3$ receptor antagonist, on electrically induced convulsions in mice", European Journal of Pharmacology, vol. 234, pp. 129-133 (1993).

Ichinose M. et al., "Histamine $H_3$-receptors inhibit cholinergic neurotransmission in guinea-pig airways", Br. J. Pharmacol., vol. 97, pp. 13-15 (1989).

Phillips J. et al., "Chapter 4. Recent Advances in Histamine $H_3$ Receptor Agents", Annual Reports in Medical Chemistry, vol. 33, pp. 31-40 (1998).

Endou M. et al, "Food-deprived activity stress decreased the activity of the histaminergic neuron system in rats" Brain Research 891:32-41 (2001).

Attoub et al., "The $H_3$ Receptor Is Involved in Cholecystokinin Inhibition of Food Intake in Rats," Life Sci., 69:469-478 (2001).

Lecklin et al., "The Blockade of $H_1$ Receptors Attenuates the Suppression of Feeding and Diuresis Induced by Inhibition of Histamine Catabloism," Pharmacol. Biochem. Behav., 59:753-758 (1998).

Sakata et al, "Hypothalamic Neuronal Histamine: Implications of its Homeostatic Control of Energy Metabolism," Nutrition 13:403-411 (1997).

* cited by examiner

SEQUENCE LISTING

```
<160> NUMBER OF SEQ ID NOS: 1

<210> SEQ ID NO 1
<211> LENGTH: 18105
<212> TYPE: DNA
<213> ORGANISM: Mus musculus
<220> FEATURE:
<221> NAME/KEY: misc_feature
<222> LOCATION: (1)...(18105)
<223> OTHER INFORMATION: n = A,T,C or G

<400> SEQUENCE: 1
atggagcgcg cgccgcccga cgggctgatg aacgcgtcgg gcgctctggc cggagaggcg      60
gcggctgcag gcggggcgcg cggcttctcg gctgcctgga ccgctgtcct ggctgcgctc     120
atggcgctgc tcatcgtggc cacagtgctg ggcaacgcgc tggtcatgct cgccttcgtg     180
gcggattcga gcctccgcac ccagaacaac ttctttctgc tcaacctcgc catctccgac     240
ttcctcgtgg gtgccttctg catcccattg tatgtaccct atgtgctgac cggccgttgg     300
acctttggcc ggggcctctg caagctgtgg ctggtggtag actacctact gtgtgcctcc     360
tcagtcttca acatcgtgct gatcagctat gaccgattcc tgtcagtcac tcgagctgtc     420
tcctacaggg cccagcaggg ggacacaaga cgggctgttc ggaagatggc actggtgtgg     480
gtgctggcct tcctgctgta tgggcctgcc atcctgagtt gggagtacct gtccggtggc     540
agctccatcc ccgagggcca ctgctatgct gagttcttct acaactggta ctttctcatc     600
acggcctcca ccctcgagtt cttcacaccc ttcctcagcg ttaccttctt caacctcagc     660
atctacctga acatccagag gcgcactcgt cttcggctgg atggggccg agaggctggt     720 ccagaacccc cacctgatgc ccaaccctcg ccacctccag ctcccccag ctgctgggc      780 tgctggccaa aggggcacgg ggaggccatg ccattgcaca ggtatggggt gggtgaggca     840
ggccctggtg ttgagactgg ggaggctggc ctcgggggtg gcagcggtgg aggcgctgct     900
gcctcgccta cctccagctc cggcagctcc tcaaggggca ctgagaggcc acgctcactc     960 aaaagggct ccaagccatc agcgtcttca gcgtccttgg agaagcgcat gaagatggta    1020
tcccaaagca tcacccagcg ctttcggctg tcgcgggaca agaaggtagc caagtcgctg    1080
gctatcatcg tgagcatctt tgggctctgc tgggccccgt acacactcct catgatcatc    1140
cgggctgctt gccatggcca ctgcgtcccc gactactggt acgagacgtc cttctggctt    1200
ctgtgggcca actcggccgt caacccccgtc ctctaccac tgtgccacta cagcttccgt    1260
agagccttca ccaagctcct ctgccccag aagctcaagg tccagcccca tggctccctg    1320
gagcagtgct ggaagtgabg gnmcdnasnc cgactcgatc ctgaggtca agccaactct    1380 gagggcttag aatggaggcc agaggctccc tgacagaatc cctctgtctt cttgactagg    1440
gcgggaacta ccccttcctc aagggtgggc catctgcctg tgtcttgcaa gacccacgca    1500
aggcctccct tgaccacagc tggcgctgtg ggtggtcaca gccagatagc aacacgaacc    1560
```

```
ccatcatcct gttttccatc ctcaccoctg acggaggcag aacagagatg atcgctcccc    1620
attccagaag ggaaactaag gctcaagagc agcagctcgc ccagggacag gctaccaacc    1680
acccaccctc tgcccttcac ccactccact cttacctctt tgccagaatg ctatctcttc    1740
atctcagcct gttttgtccgc cagctgggcc agggtgtggc atccaggaac tggggtgcct    1800
tgtatgtggc cccacctggc ccctgctgct gaagccagcc tgaggccatc tccaccccag    1860
attcccaggt ccctggcaga acacacttcc agctctcttc tcagccatgc catggaatct    1920
tccgtgggga caggaagtag gctgccagtg ggcagcctga ccacagaggc ctggaccggc    1980
tcacgtggct cggctgattc ttctcagtca actttcaagt ctcctctgca acgtgacgat    2040
gctggcttcc ctgtcgggga gggtgggtat ttttaggttg aacccgcctc gtgaagagac    2100
aagttatcaa tagcagcaga aaagggcttt ttcttattct ttttcccct gtggctttgg     2160
gacacgaaca agctgcacct attaaactct gccaaaagga agcaggaaaa gtggtgttcc    2220
ccattaaact tttcaccccca aagttccttc tatgtgacag caagcccaag ccatcccagg   2280
ctaaccccaa cactccttcc tctttgggaa agctacccta caaccttcc tagtgacagg    2340
tcctgtagag gtcaaggagt gaggatccag aggaggtgga aaaggaggcc ccacagactc    2400
ccttctaagc accaaggaag ctactggccc gtttctcatt tcccagttct gtgtgcccca   2460
ctgtaggctg agtgccctag agtggattgt gtcagctaaa tgctcaacta ctcatggcaa   2520
gtgatcagga ggcccccagg agtctgccta cctgaggtca ggaggcctca cttgctagtt    2580
agctactgtt tcctgagatc agagggatgt gtgaaaaacc ggtcaaagcc agcacgcttc   2640
ttcctcccccc acaaggctga ccagagtgtg tggaggcgcc tgcacgcaaa gagcccagct   2700
cagacccagc atgtgcgaac actgagattt tcttgacagg tcactagaat ggcatcctgc    2760
cttgctgaag gaaacatttg agccgacttg gctgcctgcc cttcaggaat ggttagcaag    2820
cactccattt ctgaagaagc ccagaataac aaaggcttca acaaaataga agtgtgcttg   2880
ctcccatgtg acaggagccc aagctgccct gtctcactcc tgctttgctg tataactcaa   2940
caaaggttcc ttccagtctc atgtcacgcc atggcccaaa acagtggctg gtgctctaat   3000
catcacacac agctctaacc agaaaggaag ggatgaaaag agggaggaag gataacattg    3060
ctgctcccgc ccccaagata aatcagcttg aaaatctgcc ccaggagctg aggaaagttc    3120
agccagtgaa ccagtgtgtc cctcttccca gctgtactct gactggtgga aagtgggttt    3180
ctctctcttt tcccaacatc catttctcca cttacacttc actagccagg acaccatccc    3240
ctgctacttt gacaaggctg aagcattcta cctgagggtg tcactggcct aagtaaaaca    3300
ggctcagaag agatgattac agtggtcact tgcctagtag gcctacctgc tggcctcacc   3360
ttgagtagtg tctgagactg tccaccccca cccaggcccc aggggctggg acttcaaccc   3420
ccacacacac atacactaaa gcccataaca atggaattcc acgatacccct cctgggccag   3480
tgtgggacgg atgccagcca gactccatct catagtcttt agggcaactc catacccagc    3540
atggagctgg cccagggaac tatggttcct tcttcctggc tgtactggag ctgatggaag    3600
atgggtccct gtctttcttc ccagtatccc ctgagcacct gccacacact gaccctgcct   3660
tggaccctga acacagatgc agaatacacc tgagcaaaga gaggtcccgg atcctggtct    3720
aggatccaca agtcccaggg acccatatcg ggtggcaaga atatacgcac atcctcgtgc   3780
agggaactgg cagggcagga gagaactgga ggagcgacag ctgggctggg ttagatttag   3840
cttgctgaga gccaaatgcg ttggccggag ccgctggctg ggcctcggtg ccagggaagc   3900
tgcataccgg atgggagggg caggttaaac acgcctgggg agcctagatg gagagcagag   3960
```

```
atgaggctca ggacagagaa tggaggtttc ttctttccgg tagtagccca ggccagggag    4020
gaaggctagc caaggccacc ctccctccct ccctggcacc agcatgcttc ctccataagg    4080
tggagctaag gacatagggg aaaggcaacc tggtaactgg agtccttctg ggagagggta    4140
tgcacccttt ccccatcttg ggagaggcag tcaaaaaaga cacagcctgc cggggcgtag    4200
tggcacatgc ctttaatccc agcactcggg aggcagagac aggtggattt ctgagtttga    4260
ggccagcctg gtctacaaag tgagttccag gacagccagg gctatacaga gaaaccctgt    4320
ctctaaaaaa aacaaaaaca aaataaaaa acaaaaaaca aagaaagaca cagccaagga    4380
cctagtggcc actgcctgtg tgccgggctg ggttaccaca gaggtcaggt gccctgccct    4440
ggctcctgac ctgtggttga gaggatgtgg tagtctctca cagtgttcta gtctagccag    4500
gagcctccat ggaagcaagc ctatgccagt gtgcaagacc caagctggat ttactgcact    4560
ggtatcacta tcttgaaatt cttcggccac atttccttct catagcaaaa tgtacagcca    4620
cgctatagaa ggagtgggct gggcaatggc taattcccca accagctccg tgacttatcc    4680
cctgcaggga tggggatggg ccaggctatc aggttgaggt tgtttgggga agatctggag    4740
gggcttataa agggcctcat tctggtcgtg ttgccaaggc tgggagaagt caggaaatcc    4800
aagacaacct tagccatgac tctaaagtga ctcagggata ggcctcccca gagcacccct    4860
ggaagacaga gttagctcag ggcttcccca atacctggc ctgaagagca gcctggcctt    4920
ctgagccctt ggcaatagga gatggtgcaa gtagatccta cagacaaccc aggaaggaca    4980
gagcccagtg tccacatggg atgggttttt acctgtcatt tgctctgtgt gcctccatct    5040
tcctggggct tgggaaggta tgtgaaaacc ttccgagggc accggtcat ctgcacagga    5100 tccatctagg agctacctag actcctcccc atcagcaggc tgacctcaga caggtgcact    5160
tgaaagccag atgcagggtt tgagtacaga cccttacct accctggac tgtgtgttga    5220 gatatgagcc taaaggtgac accccaagga gagaggctcg ccaggagagc agagtcaaga    5280
ggacaaggta gcagttaggc tcctaaagcc agccattcct aacgaggtgg atgaaatgac    5340
ccactttctc cactgggcat gcctggccag gatccccctt caaaatgtca tacaagtcaa    5400
gagtagtgac acctttagtc ccagcacttg gggagggaga agcaggtgga tctctgtgag    5460
ttaaaagcca gcctggtcta catagagaga cccttctcc aaacaaacaa acaaacaaac    5520
aaacaaacaa acaaacaaaa gacagagtct agcctccttc tcagttatca ggctcagcac    5580
tgccgcttcc cacacatgac cactgttgtc ccaactggaa caggtaagca ctagctccgc    5640
ccggctgagt tctgtggagc aacagcttca tctgtcagca acctgtgcaa gccctcatag    5700
gtgccagtcc ccactccaaa gcccaccacc agcacctcag ccccactgtc ttacacaagt    5760
ctgggggcct taggagacac cctgttatgt tttcctgttg tgtcctgact gtgtgggcta    5820
tgagcatgtc agataaatgg atgaatgtgt gggatgcagg tatcagcaag gatctcagac    5880
acccacccag ccatcctagg cctctatgga gataggacat attcctgtta ccagcttgtc    5940
tctacagctc aggtcagatt catcctgttg taaccttaca cacacacaca cacacaaa    6000 cactctctct acctactccc tctctctctc ccccgacccc gccagcttct gaggcccat    6060 ccttcctctc ttgaggagcc aaagactcgc cttcattaat tgcattctca gccctaccct    6120
gagcagttcc tcccatctct attttcctgg cagggatctg ttccccaagg agctgcctgg    6180
actcccaggg gacatcaaga gtaaacagag ccaccttaca gagggcaggg tcttccaagc    6240
agtcctaagc caacagtcac tcaacttcct tttattttta tttttaaac tgtgtttctg    6300
```

```
agggctgtag agagggctca gggctctaag aggagttgag gagtccacat aactctgggg    6360
tgggggttgg gggctgggca tattcacaga agtatgagca ccacacaggt cacagggcac    6420 aatgggaac cctggagaaa ccctgagggc accctctggg gtgctggttg gctgaccctg     6480
atgtgactgg gaggggtttt cctatggggt gcataacagc taaccccact agcatccgtg    6540
ctccagctgg gtagagtgct cttctgccca gcagttagac tccaggacaa gcccagtggg    6600
ccagtccagc agactctccc ccaaccagga caggggaaaa atggacaggg gatgcctggt    6660
cctcccatga ccttaggtgc tgagaagagg acattcgttg gctacatgga gtagcctgat    6720
atgattagtc cccaacttga ccatctagtc ttgcaccatc agactggggt ctacatcaga    6780
ggcaagagtc accttgtcat ggtgttgtca catgtagagt gactgcagtg gggtgcagga    6840
gatggtcaag cagagggcag gaacccagag atatcagaag ataaagcatt caggctggac    6900
aaggccatga tggcagtcaa acatacagga tatggaacct agacctttag agaagatggg    6960
aatttccaga acagagagca ggttaccaga cacagccaga cacaggtcaa gagttcagac    7020
agaggcccag cattgcggta cagactttta atcccagcac tgagggatca gagacaggtg    7080
ggtctctcag tttaaggtca attgggtctg cagagtgagt tccaggtagc tagaactata    7140
cagagaaacc ctgtctcaaa cctcccctttc cccaaagact ctagacagag gaatgtctta    7200
gacctaccta gcaggaacca ggccaagggc atggaggagc tcaatgtggg tactaactgg    7260
gctgttggga gaggactcag tgaagacagg cagagttgaa cagatcacaa gaggctgtgc    7320
ctcctttctc tccagagcag ggccctccat catagcacct gtccccatct ctagagatga    7380
agaggtctga gaactggcca gtgccccttt gttgtgtgac agtcaccatt cacagctgcc    7440
tagaacaagc cacagtctga tggcccagag agagcactga catgaagagg tttggagctt    7500
ggctgagtcg gtaggcaggc ttaatgttgt cacagcatag tctgggaggc ttcactaaac    7560
actccaggga aagaattaga ggcttctggc catgggctgg gctccatacc atcatagggc    7620
cccacaccag cccatattct gcctggaagc cctggaggct ctctgcagta gggctgcttc    7680
cacttctctc cggctttcct gtgtggttgt cttggactta gcactcaaag gacaagatgc    7740
ctgcaggtgc cagggctgag gtcaaacagc tacaagtact catcaactac ccagactctg    7800
agagtgctaa catggtctgt agtgtcacct caggggacaa gtggccttcc aagactctgt    7860
cttctgttat gccacaacag cttctccagt agcttcactg tcagctgtga catcactctc    7920
tgtattaccc tataggcagt gtggacccag gttctcagaa acttggcaca gctgccccaa    7980
gaccccacta cagtacctgt tctgccgagg tcatgtctct gagagacggt gtgtgagctc    8040
ctgataccag cactggctac ttggctgaat ggccatccca agggcagctg cagaggtaac    8100
tgattgcaac caggcttgcc aacaactccc cacctctgtt ttctccctgg tcattatgga    8160
gtttgaatta tgtacaccca caccacggcc agggcagcta catgactgtc ataaacagac    8220
taatgtggca gactcttaag acagagagaa gggaacagga actggaggga gccgcaggga    8280
gagatttcag ggacagtctg ggaaggaggc aaacacagag gaggtaagct ggaaaagaag    8340
gttgtctttg agcaccccga gtctcatctt tcctggactt ttgagcccta ggcaacaaca    8400
gtcatgtctt tctttaagga tttcttgaat tagtctttgt cacgttcaac taaacagcaa    8460
cactatctcc catctccttt ttcctctctg acatctggtc cctaaaggtg acatggagag    8520
tcagaccctg tgtctgttct gcatcatggc ctcagacgcc tttttttatca catttgggcc    8580 ctgagctcat cagggtgcac ccggagctgg ctcagaatgt cacggatgg ggggttggg      8640 gggagggggg agccaaggaa caaaaaaaga aaaatctgca ttcccatatt caaatgagct    8700
```

```
cctgcaggcg ggagcagaca gcaggtccac tgaggaaatg aaacattgag aggccaggcc    8760
ctggcaagca acttgcccac tacaggccgg acggctgccc ttcaactagc ccttggtggt    8820
tcctgttctc tctcgttatt tctcattagt gagcagtgtt cccacacagc acaggcaaaa    8880
gctctgcagc cagtcgcacc aggatcaccc ttagttcaag ggagaaaggt cttttctggc    8940
aacgaggaaa agagctggag gcagaaagcc gcctgggaca gcatgggagg atggcaccag    9000
ctaagctgag gccgtgacct gcactggctt cttcagccca gagctgctcc tcccctggtc    9060
cccagccatg tgttccagct atccttttga gtgtgactgc acctcagtct tgtaacgttc    9120
aacacccaac acccagattc ccactcagct ccacgacacg gctgcaaact ctgccctgtg    9180
gagagcttga accctaaact ctggaggtag gctgggccta cctctttccc ctcccctccc    9240
acagcttatg ccaggcttga aaaacatcc aaagtcttca ggtccccact tggacttcat     9300
tacacaactg cctccagctg gctctgggca tctaccctcc accctcccag ttaaccccac    9360
tgtggccagg aacctttaag aggactctcg gagttccaag gaaacaccag catcctgccc    9420
gctgcatgag aagcctaccc cctttccttc caaagccctc ccatctgtct ttctgtgctt    9480
cagcctaact ggcttcctgg ctgccttaca ctggcccacc cttttctgct gctatcccca    9540
accccaaacc tccatttcct tcctctcctc tccatgtctg tgacctagtg acatcttgtc    9600
agtgagaaat ccctttaaaa atccgagtct ggccctagtt gaagtcgggt tcaccagtta    9660
aggcaggact ggaggtgaag acagtgacct atgaaagaga ccttggcagg tggccagagc    9720
cactccctga tgtccttagc tgcgggtccc ttggcccgag gagcttcaga gatgaggact    9780
cctatcccag acgatccctg aacaacatat tctctgatgg gttattgaaa gggatttggg    9840
gggtggcttt ttccccccac caactccagt tcctagacac tgtgcctgtc ccctgcaagt    9900
acagtaccgt agaaatgcct ctgacccata gtatatatcc tataggaagg caagtatcct    9960
catcggccat tgtccccagc ctgtgtgcct agaggaggct ggaactgcag cctatgatgt   10020
tcttccaggg tgtgggctac tagtcttgga tcactcctag cctcttttgc agaaaactag   10080
tctcttggcc agatgctgca tacgcatacc cgtgcccatg ggcggggact atgcaagctc   10140
ttgcatgtgg cttaggctga gttagcaagg gtggcctgaa ccgggagaag gaggccacga   10200
agttagctca ttaccaggta tgagggctat ttgtttggag tttgtttttg ggatgggtcc   10260
gtggccaggc attcagaaaa acaagagttt agcatatggg attacagctt tagggcccac   10320
gggagcctcc aatgtggcca ctgcgttgtg ctaacatgcc agtctgtaag gtacactctg   10380
ggggtgcatc tggccttgtg ttccttttcc tacacaaagc ccttcctggg aaaatcctcc   10440
agggtagggt gccacatagt gaccttcctt acttatgcat tgccttggtc caattggcca   10500
gtcaagtttc tctgcctgca tgcttcttac acttgtattt ctactggcct caggagactc   10560
tatctcaggg ctgaaccagg actagggccc tggagagggt gaactctacg tctgtggggc   10620
cctatgcaga tgattctaca tagggcagtg gttctcaacc tttctaatgc tgtgacccttt  10680 taatacagtt gcttatgttg tggttacccc caaccataaa attattttgt tgctacttca   10740
taagtgtaat tttgctactg taacgaatca cagtataaac atctgatagg caggatatct   10800
gatatgtgac cccccaaagg ggttgcaatc cccaggttga gaaacactga catagggtgt   10860
ctgggagcct aatgaggtca tgcatacaag cagtgagtct ggcctatagg gggcacccat   10920
aaccaccgcc actgtcctta tcaaacctct gggctaactt aaccttcctg cttcttctgg   10980
cctccatttg tggaggaaga tttccaagct cccagagact gggtagcttc ctccaagagc   11040
```

-continued

```
atagctgaac cttcaatgct agggtctgaa gtgatcctag ttaagtgtcg ttatggagct   11100
tggccccgtc agaatctcta ggagtgtgca gggatctggc ttgtaggaca tgatgcatac   11160
tgcctgtttt tgtttgtttg ttcgtttgtt tttaatgtat gttgaacatt ccatgacacc   11220
agtacagcag caccatagac agctgtgggg cagtggagtt gaatagggtt aaattgggtc   11280
cacctagctg ctggaatagt aacaaaccac cagggaactg ctctttgtcc caagtggtct   11340
ccaggtggtt ctctgggggt gggcaacaag cagcaacatt catggaggcc tggataggcg   11400
cacatgaagg aagggagaca tagctggtga gtctccatgt cacatagtcc tgagttcttc   11460
atagggtccc agcctccact tatcagaata atgaccaata ccagggcact ttagactagg   11520
atggggtggg gggtgggggga ggctggtgag atggctcagt gggtaagaac actgactgct   11580
cttctgaagg tcctgagttc aaatcccaac aaccacatgg tggctcacaa ccatccacag   11640
tgagatctaa cgctctcttc tggcatgtct gaagacagct acagtgtact tatttataat   11700
aataaataag tctttgggtc agagagagca gggttgacca gagtgagcag aggtcctaaa   11760
ttcaattccc aacaaccaga tgaagctcac aactacacaa ctatctgtac agctacagtg   11820
tatacacata tacataaaat aaacaaataa atctttaaaa aaaacaaaaa acaaaaaacc   11880
aagactggga ccggaactgg ccaagacttt atagggattt tacaaatttt tattgactct   11940
catcctcaat cctgtgtcaa gatggggaca ttcagccatt aatgagatct aaagatccct   12000
ttaaattccc tcccaacccc atttcctgag ggctctgaga tttctgagca acatgtccgg   12060
ttctactcac tttcacggga agaaagagag cagctgaaag aagcattttg gaggtgctgc   12120
acagtactgg gagagtgagc cctgccaagc ccttcaggcc acacacaggc ttgaagggca   12180
ggcttgattg tacccaccag ttcagctgga tcttgctgtc cagttccagg acatgttact   12240
ttgacctcta gttaagtgcc tgaacccagt gcagcctctg gacacagtca gtgtgctgtg   12300
gagggggagcc gaaggtttgc ttgtaagagc agatcagaga aggctttctg gagacgatac   12360
attggaattt acccctcccc catagaagct tccagggtgc ctttgggggg ctgagactat   12420
gggcttgggg tagaggctcc tctttgccag catcccaag gctggaacag agaaatgcca   12480
gtccccactg cccaaagttc tcagagaacc acttggggtg ggggaggggc aggtcctcac   12540
atgaccagcc tctggctgtc agtgtggggt gcttgaagcg gtgcctgggg tcccctcc   12600
ccacactcat accgtctaca tttctgtcca ctttgaggca tccactgatg tgtgctgttg   12660
gtgacagagg acagtcactg cttcccctct ccctcgggca ctgttctctg tctgtctgct   12720
gtctgactat tcgtgggtcc cagcctgatg ctgggtggct gtttccctga atgtgaatgt   12780
ctgtgtgtca gagcgtgggt gtgtctgtct gtcttcaggg agcctctgct gctgactctg   12840
tccttgacct ccagtatctg tgtcagagaa gggggggccgg cggctttcct cctcccctc   12900
ccacaggcac taacgcagct gccaccaccc cggctgcacc cagaactcag tgacctcacc   12960
tgtcccctgc agcagtgacc accccactaa ggtatctcag ggggcattcg tggcccgaac   13020
caagctgctt tgtgggtcgc ccctccaccc actgccgctg agttctgggt gaatgttctc   13080
agctctgggc tgggtccgct caggctcgtt cttcccttat gtaactccac atctgtgtgt   13140
gccttgcagg tcaccctgga ccctgttctg agctctgtct aaccacgtgg agattgagac   13200
cccacagttc tgtgcatatg aggctggaga gaaccctgt tcccggcatc actttcaggg   13260
accctctccc aatctttctt tggacatctc ttaccccaga aacctacttg cccaaagcaa   13320
gatgcgaaag ggagtcctga ggcgcaagtt cctagagct gcgggcagc cattctccac   13380
cccaccccggg cagtgtccta ggtcctgaca agcttaggag ctacggacaa gggtcgggca   13440
```

```
ggggtcacca ggggcgaggg cacgagggcg aacggatagc caagggacca gcttctaggt   13500
gcgacctcag acatggatgc tgcaggagac cggggcaggg gttctagtcg gccggcgggc   13560
acgcggcgct gtccgtggtg ctgcccgcgc cgggcggggc ggaggcggga cggaggcggg   13620
gcgagggcgc cagccaatgg cgggggctct gcgcggggcg cggggggcgg cgggccgatc   13680
gcggggcgca cttggctgcg cgctgagcta ggggtgcacc gacgcgccgc gggcggctgg   13740
agctcggctt tgctctcgct gcagcagccg cgcacccgcc ccactctgct cagattccga   13800
taccagcccc ctctgcatca ccctcccgga ctccagactc ggctctcgct ccggtcccgc   13860
ggaccatgct ccgggcgccc cccggaaaac cgggctgggt gaagagccgg caaagattag   13920
gctcaagagc aggggccccg ccccggccac cagcactcgg cccctgccct gcccagtgtc   13980
cccgagccct gtgagcctgc tgggccatgg agcgcgcgcc gcccgacggg ctgatgaacg   14040
cgtcgggcgc tctggccgga gaggcggcgg ctgcaggcgg ggcgcgcggc ttctcggctg   14100
cctggaccgc tgtcctggct gcgctcatgg cgctgctcat cgtggccaca gtgctgggca   14160
acgcgctggt catgctcgcc ttcgtggcgg attcgagcct ccgcacccag aacaacttct   14220
ttctgctcaa cctcgccatc tccgacttcc tcgtgggtaa agcccccaga ccctgtccgc   14280
tgccagartc caggggcgcg gasccgggc tgggcaatgg ggcttggcgc ttcgacctgg   14340
ggtggcttct caggggttcg gccttgggag aggagctcta gaaaccttag gatggtgggc   14400
gcgggagaag ttcctcgcct cccgggccgc aagacggggg ctaggtaggg atgtccccgg   14460
ggaggctgcc ccagccggcg ggcgctcagc aaggcgcaag gcgcagcgac cgccggtgca   14520
gcgttggctc ctgcgccgaa ccaaacaaag gcagcggcgc cggactcagg atgctgggag   14580
gacgctgggg gggaggggac atggaarggg gatttgggga ggtgtgctgg ggaaggggac   14640
cgtarggaar gcgggggtk agatgaggga aatgctccga ggagctcgtt ctcacgtgtc   14700
caagctctgc tcccaactgg gggagggggg gcggggctcg cggtggggc cggagcgcca   14760 gacacctgtt ggggctgcga gctgctgcgt ctcccagacg ctggaagccg gtttgggcgg   14820
tgagagcggc tggcgcggct gcagccaaga acccttaag ccaagagaaa agctttctcg   14880
gtttttaagc tgagaaggga ggctgtccaa cagccagggt agagatggat gatcggctcc   14940
agagccaatc aagccaggga ggacatatat cccattttcc tcttttggcg gttggtgggg   15000
ctggcagaag cccaggtttt gtgttcagag gtccctatgt ggaggtcctt cctcctgcca   15060
ccaggtccag aagacattga tgggctggag gatggcagct gctcagttgt aggggggacag   15120 ggtgactagg aggataaata agatatagta ctagccctag aaaggtggct accctatgaa   15180
ggccaggctc tgccctttct ctatgtggtc agtctgaccc cagctcttga gccatggtcc   15240
caccacagct gctttcctat aggtgccttc tgcatcccat tgtatgtacc ctatgtgctg   15300 accgccgtt ggacctttgg ccggggcctc tgcaagctgt ggctggtggt agactaccta   15360
ctgtgtgcct cctcagtctt caacatcgtg ctgatcagct atgaccgatt cctgtcagtc   15420
actcgagctg tgagttctgg gatgtgggca ttagagttta ccctgtgtgt cggagagcac   15480
tggacagggt atggctgctc ctgagttata ggcagatggt cttgctccct tttgaccggt   15540
gggccatttt tctgtgaccg ttggctgcca gtagtagtac tagcatgagg caggaggttg   15600
gcttggaatt ccatactatt gcagaaaggg gtgtcagggt ccatcctcta tcctggacag   15660
gtacaggatt cctggaactg aaggagggtc ttcatcctc ccactttgt gtgcatgaag   15720 gcgtgctcac ataacaccag gaagccgcag tccctaactg cacacgctcc cctaaatggc   15780
```

```
tgttgtaaga tagctctggg acccaggcag agggagagga ggacactggt gtggagtggg   15840
ggtccatctc ccacttcccc aactcctctt ctcagtggct cactcccttc aggttttgtc   15900
aggatgcatc ctgaggatgc ttgcaaagag caccagcatg gagccctctt gagcttccct   15960
aggtcccctg taccatcccc tgaaccacag ggctattgtg actaaggtgc ccagtacagt   16020
gctggcatgt ggcatgtgta ccctagacct gtggttagct tgtgtggttc ccaaggtggc   16080
tgtcaaggac acttgtctca gctgtccctc tgaggcccct tagcaggatt tttgcccct    16140
cctgccaccc ttcccttgc ttactcagcg cacttggagc ttactttgtt tcttggaaaa    16200
agactagatg gtcccacctt cctacctttt ctagccattc accttctaga aagaagaca    16260
gactatttaa tttttgtggg gtggggtggg gtgggaggag tctctagcag tgggccagca   16320
ggtttccctt ctgtattccc agctccagta gtgagaggaa ggaaatactg gtgcagagtt   16380
gggacaaagc ccttcccttt cagcacagca aaccgttgaa gacagctctc tggcccttgc   16440
aagaagcctc acatcagaaa cagttgtgtg tggcctctgg gtgtggccag tgctaatgac   16500
acaagcaaag tcaggggac cccatggagc tggtggagga tgatgaagag acaggattct    16560
ggttggttgt ggtaggctct gaggctctgg gagaatgtgt gggcatcagg caggcagggg   16620
acacaagcag gggagagaag gaacatggca ccttacccag agcagacacg gaagctgagg   16680
cttctctgat cctccagtcc aatgctgctg acctgttgtt gatctgtaca aaccactgca   16740
ggtctcctac cgggcccagc aggggacac aagacgggct gttcggaaga tggcactggt    16800
gtgggtgctg gccttcctgc tgtatgggcc tgccatcctg agttgggagt acctgtccgg   16860
tggcagctcc atccccgagg ccactgcta tgctgagttc ttctacaact ggtactttct    16920
catcacggcc tccaccctcg agttcttcac acccttcctc agcgttacct tcttcaacct   16980
cagcatctac ctgaacatcc agaggcgcac tcgtcttcgg ctggatgggg gccgagaggc   17040
tggtccagaa ccccccacctg atgcccaacc ctcgccacct ccagctcccc ccagctgctg   17100
gggctgctgg ccaaagggc acggggaggc catgccattg cacaggtatg gggtgggtga    17160
ggcaggccct ggtgttgaga ctggggaggc tggcctcggg ggtggcagcg gtggaggcgc   17220
tgctgcctcg cctacctcca gctccggcag ctcctcaagg ggcactgaga ggccacgctc   17280
actcaaaagg ggctccaagc catcagcgtc ttcagcgtcc ttggagaagc gcatgaagat   17340
ggtatcccaa agcatcaccc agcgctttcg gctgtcgcgg gacaagaagg tagccaagtc   17400
gctggctatc atcgtgagca tctttgggct ctgctgggcc ccgtacacac tcctcatgat   17460
catccgggct gcttgccatg gccactgcgt ccccgactac tggtacgaga cgtccttctg   17520
gcttctgtgg gccaactcgg ccgtcaaccc cgtcctctac ccactgtgcc actacagctt   17580
ccgtagagcc ttcaccaagc tcctctgccc ccagaagctc aaggtccagc ccatggctc    17640
cctggagcag tgctggaagt gagcagctgc mmmaccctc tacggccagg cccttgtacc    17700
tgttctgagg gggagcccga gcgtgggccc tgcctttgtc cggggtctgc tccaaatgcc   17760
atggcagcct cttagagcat caacccggca gtggggcagc atggtaggag ggccaagagc   17820
cctcgttggt ggaactggag tgtgctggct ggctttgccg ccacattctc cttcacccca   17880
gaagagacaa tccgggagtc ccaggcatgc cttccacctc cacacactca gtgcagtgcc   17940
agtgatgtcc tcctttgcat acttagtggt tggtgtcctc cctaatgcaa accttggtgt   18000
gtgctcccag ctcctgccct ggcaatgcgc cctgcatgtg cacacacctg ccacttccac   18060
cacacacttg caataccttc tctctcccaa gacgatcgag tcgac                   18105
```

UTILIZATION OF HISTAMINE RECEPTOR H3 GENE PARTICIPATING IN BODY WEIGHT OR FOOD INTAKE CONTROL

CROSS-REFERENCE TO RELATED APPLICATIONS

This application is the national phase application under 35 U.S.C. §371 of PCT International Application No. PCT/JP02/06580, which has an International filing date of Jun. 28, 2002, and which claims priority to Japanese Application Serial No. 2001-201413, filed Jul. 2, 2001. The contents of these applications are incorporated by reference in their entirety.

TECHNICAL FIELD

The present invention relates to pharmaceutical agents for treatment or prevention of diseases exhibiting changes in body weight or food intake, methods of screening for candidate compounds thereof, as well as methods and agents for examining diseases exhibiting changes in body weight or food intake. Furthermore, the present invention relates to nonhuman higher animal cells and nonhuman higher animals which can be used in the screening, and in which expression of the histamine receptor H3 gene is artificially inhibited.

BACKGROUND ART

Many hormones and neurotransmitters regulate biological functions via specific receptor proteins on the cell membrane. Most of these receptor proteins carry out intracellular signaling via the activation of coupled guanosine triphosphate-binding proteins (G proteins). These receptor proteins are collectively called "G protein-coupled receptor proteins", or "seven-transmembrane receptor proteins", owing to their common structure comprising seven transmembrane domains.

G protein-coupled receptor proteins exist on the surface of living cells and various functional cells in organs. These receptor proteins play exceedingly important roles as targets of various molecules that regulate the functions of cells and organs, for example, hormones, neurotransmitters, physiologically active substances and such. Therefore, G protein-coupled receptor proteins have attracted attention as targets in developing pharmaceutical agents.

Histamine receptor H3 protein is a type of G protein-coupled receptor protein. Genes encoding the protein have been reported in various organisms including humans (Lovenberg T. W. et al., Molecular Pharmacology, 55: 1101-1107, 1999; Lovenberg T. W. et al., Journal of Pharmacology and Experimental Therapeutics, 293: 771-778, 2000; Tardivel-Lacombe J. et al., Molecular Neuroscience 11: 755-759, 2000).

To date, analysis of the action mechanism of the histamine receptor H3 protein has been carried out using its agonists and antagonists.

Administering cats with R-α-methylhistamine (RAMH), a histamine receptor H3 protein agonist, causes a significant increase in deep slow-wave sleep. This effect is reversed by administration of thioperamide, a histamine receptor H3 protein antagonist. Conversely, waking effects were observed upon thioperamide administration, an effect antagonized by RAMH. Thus the histamine receptor H3 protein may be involved with sleep (Lin J. S. et al., Neuropharmacology 27: 111-122, 1988).

Administration of RAMH decreases voluntary movement in rats and mice. Conversely, thioperamide exhibits anxiety-inducing effects in mice. PET scans show high concentrations of histamine receptor H3 protein at a site in the brain considered to be related to attention deficit hyperactivity disorder (ADHD). Furthermore, drugs comprising sedative or anti-anxiety effects, such as clinidine (α-2 agonist), 8-OH-DPAT (acts on 5HT), diazepam, and buspirone, have been reported to reduce histamine neuron metabolic turnover. Therefore, histamine receptor H3 protein may be involved with antianxiety effects (Schwartz J. C. et al., Histaminergic Neurons: Morphology and Function. CRC Press 85-104, 1991).

There are many reports that activation of histamine neurons leads to improvement of memory and learning, while histamine receptor H1 protein antagonists and histamine biosynthesis inhibitors cause their deterioration. Furthermore, in human Alzheimer's disease patients, histamine levels in the cerebrospinal fluid are reduced. This is also observed in Down's syndrome patients, and is considered a common phenomenon among patients with learning disabilities. Thioperamide exhibits an effect in improving learning in senescence-accelerated mice with learning disabilities. Thioperamide also shows both histamine dissociation and acetylcholine dissociation promoting activity. Therefore, the histamine receptor H3 protein may be involved with memory and learning functions (Mochizuki T. et al., Naunyn-Schmiedberg's Archieves Pharmacology 343: 190-195, 1991).

Intracerebral administration of histamine to mice results in analgesic and/or algesic action, depending on the dose. Histamine receptor H1 protein antagonists show potentiation of morphine's analgesic effect, whilst histamine receptor H2 protein antagonists show attenuation. Thioperamide administration shows attenuation of analgesia, due to stimulation of the histamine receptor H1 protein. Since the analgesic effect of thioperamide is antagonized by RAMH, the histamine receptor H3 protein may be involved with analgesic effects (Onodera K. et al., Progress in Neurobiology 42: 685-702, 1994).

Histamine receptor H3 protein agonists are reported to constrict blood vessels and may therefore be effective towards pain such as human migraine headaches, which result from cerebrovascular dilation. Histamine receptor H3 protein is expressed in primary afferent sensory neurons (C-fibers). Histamine suppresses the dissociation of neuropeptides such as substance P and neurokinin. These neuropeptides act to dilate and increase the permeability of dural blood vessels, causing inflammation and pain. The histamine receptor H3 protein constricts blood vessels, and may comprise the function of being effective for pain (Mansfield L. E. Journal of Allergy and Clinical Immunology 86: 673-676, 1990).

Electroconvulsion experiments used as an experimental epilepsy model showed that histamine neurons were involved in a system for inhibiting convulsions via the histamine receptor H1 protein. Electroconvulsion can be suppressed by administration of thioperamide or Clobenpropit, which are antagonists of the histamine receptor H3 protein. These effects seem to result from dissociation of histamine by histamine receptor H3 protein agonists, and suppression of convulsions by this histamine through the histamine receptor H1 protein. Therefore, the histamine receptor H3 protein may be involved with the action of suppressing convulsions (Yokoyama H. et al., European Journal of Pharmacology 234: 129-133, 1993).

Histamine receptor H3 protein antagonists suppress gastric acid secretion by suppressing the release of histamine, acetylcholine and somatostatin from the vagus nerve, enterochromaffin-like cells and D-cells (somatostatin releasing cells). The histamine receptor H3 protein may therefore be involved with gastric acid secretion.

Histamine receptor H3 protein is expressed in primary afferent sensory nerves (C-fibers) and inhibits the release of neuropeptides by working in combination with histamine-releasing mast cells. A feedback mechanism is expressed in the respiratory system, and histamine receptor H3 protein may be involved with asthma (Ichinose M. et al., British Journal of Pharmacology 97: 13-15, 1989).

The histamine receptor H3 protein exists in sympathetic nerve endings in the circulatory system, and inhibits norepinephrine release. In chronic myocardial infarction, norepinephrine release is increased. The histamine receptor H3 protein is activated by mast cell histamines. Histamine H3 receptor protein agonists inhibit transduction in the sympathetic nervous system, and may become therapeutic agents for arrhythmia, myocardial infarction, and such. Furthermore, histamine receptor H3 protein agonists promote CGRP release. Since CGRP is increased in sepsis, heart failure, and acute myocardial infarction, such agonists may be effective for these diseases. Therefore, the histamine receptor H3 protein may be involved with circulatory function (James G. P. et al., Ann. Rep. Med. Chem. 33: 31-40, 1998).

Furthermore, administration of a histamine receptor H3 protein antagonist has been reported to reduce food intake in test animals (Ookuma K. et al., Brain Res. 628: 235-242, 1993; PCT/US94/11790).

However, studies such as those described above, using histamine receptor H3 protein agonists and antagonists, are known to influence a variety of parameters, perhaps due to compound specificity or pharmaceutical agent dose. Thus it is difficult to apply studies which use agonists and antagonists to actually determine a direct relationship between the histamine receptor H3 protein and changes in body weight or food intake.

Histamine receptor H3 protein exists at high concentrations in the feeding center, but to date there has been no report of a direct relationship between the histamine receptor H3 protein and bulimia, anorexia, or obesity.

DISCLOSURE OF THE INVENTION

The present invention has made in view of the above disclosed art. An objective of the present invention is to elucidate the function of the histamine receptor H3 protein in vivo, and to elucidate its direct relationship with diseases characterized by changes in body weight or food intake. A further objective of the present invention is to provide methods of screening for pharmaceutical agents and their candidate compounds, for treatment or prevention of such diseases, and agents and methods for examining such diseases, based on the relationship between the histamine receptor H3 protein and these diseases.

The present inventors performed extensive analyses to achieve the above-mentioned objectives. In order to elucidate the function of the histamine receptor H3 protein in vivo, the present inventors produced mice with a modified histamine receptor H3 gene. The first generation of histamine receptor H3 gene-modified mice exhibited the same phenotype as that of the control, so the present inventors used backcrossing to produce histamine receptor H3 gene-modified mice.

Body weight, food intake, blood insulin level, and blood leptin level of these mice were increased compared to the control. These results indicate that histamine receptor H3 protein comprises the function of controlling body weight, food intake, blood insulin level, and blood leptin level in vivo. Furthermore, a relationship between aberrations of the histamine receptor H3 protein and diseases characterized by changes in body weight or food intake was indicated.

Based on these findings, drug candidate compounds for treatment or prevention of diseases characterized by changes in body weight or food intake can be screened using histamine receptor H3 protein as the target. Compounds obtained by this screening are expected to be therapeutic agents for diseases characterized by changes in body weight or food intake. These diseases can also be examined by using mutant or aberrant expression of genes encoding the histamine receptor H3 protein as an indicator.

Thus the present invention relates to pharmaceutical agents for treatment or prevention of diseases caused by aberration of the histamine receptor H3 protein, methods of screening for candidate compounds thereof, as well as agents and methods for examining such diseases. The present invention specifically relates to:

[1] a pharmaceutical agent for the treatment or prevention of a disease characterized by changes in body weight or food intake, wherein said agent comprises as an active ingredient any one of (a) a DNA encoding a histamine receptor H3 protein, (b) a histamine receptor H3 protein, (c) an agonist of a histamine receptor H3 protein, and (d) an antagonist of a histamine receptor H3 protein;

[2] the pharmaceutical agent of [1], wherein the agonist is selected from the group consisting of N-α-methylhistamine, R-α-methylhistamine, BP2.94, SCH50971, SCH49648, Imitet, Immepip, GT2104, and GT5140;

[3] the pharmaceutical agent of [1], wherein the antagonist is selected from the group consisting of Clobenpropit, Ciproxifan, BP2.421, BP3.359, BP3.181, AQ-0145, UCL1390, UCL1409, UCL1199, SCH-49648, Pharmaprojects No. 5376, Pharmaprojects No. 4584, Pharmaprojects No. 4841, 4-(3-(4-Ethynylphenoxy)propyl)-1H-imidazole maleate, and GR-175737;

[4] a method of screening for a drug candidate compound for treatment or prevention of a disease characterized by changes in body weight or food intake, wherein said method comprises the steps of:

(a) contacting a test compound with a histamine receptor H3 protein;

(b) detecting binding between the histamine receptor H3 protein and the test compound; and (c) selecting a test compound that binds to the histamine receptor H3 protein;

[5] a method of screening for a drug candidate compound for treatment or prevention of a disease characterized by changes in body weight or food intake, wherein said method comprises the steps of:

(a) contacting a test compound with a cell expressing the histamine receptor H3 gene;

(b) measuring the expression level of the histamine receptor H3 gene; and (c) selecting a test compound that increases or decreases the expression level compared to the expression level detected in the absence of the test compound;

[6] a method of screening for a drug candidate compound for treatment or prevention of a disease characterized by changes in body weight or food intake, wherein said method comprises the steps of:

(a) contacting a test compound with a cell or cell extract that includes DNA comprising a structure in which a reporter gene and the transcription regulatory region of the histamine receptor H3 gene are functionally linked;

(b) measuring the expression level of the reporter gene; and (c) selecting a compound that increases or decreases the expression level of the reporter gene measured in step (b) compared to the expression level measured in the absence of the test compound;

[7] a nonhuman higher animal cell in which expression of the histamine receptor H3 gene is artificially inhibited;

[8] the nonhuman higher animal cell of [7], that is capable of differentiating into an individual, and that is characterized such that one or both genes of the histamine receptor H3 gene pair have been modified;

[9] the nonhuman higher animal cell of [7] or [8], wherein the nonhuman higher animal is a mouse;

[10] a nonhuman higher animal, wherein expression of the histamine receptor H3 gene is artificially inhibited;

[11] the nonhuman higher animal of [10], characterized such that one or both genes of the histamine receptor H3 gene pair have been modified;

[12] the nonhuman higher animal of [10] or [11], wherein increase in any one of body weight, food intake, blood insulin level, or blood leptin level is exhibited as its phenotype;

[13] the nonhuman higher animal of any one of [10] to [12], wherein the nonhuman higher animal is a rodent;

[14] the nonhuman higher animal of [13], wherein the rodent is a mouse;

[15] a nonhuman higher animal cell, wherein expression of the histamine receptor H3 gene, prepared from the nonhuman higher animal of any one of [10] to [14], is artificially inhibited;

[16] a method of screening for a drug candidate compound for treatment or prevention of a disease characterized by changes in body weight or food intake, wherein said method comprises the steps of:
(a) administering a test compound to the nonhuman higher animal of any one of [10] to [14];
(b) measuring any one of body weight, food intake, blood insulin level, or blood leptin level of the nonhuman higher animal; and
(c) selecting a test compound that changes any one of body weight, food intake, blood insulin level, or blood leptin level compared to the level measured when the test compound is not administered;

[17] a method of examining a disease characterized by changes in body weight or food intake, wherein said method comprises the step of detecting mutation of the DNA in the histamine receptor H3 gene or in the regulatory region of the said gene;

[18] the method of examining a disease characterized by changes in body weight or food intake of [17], wherein said method comprises the steps of:
(a) preparing a DNA sample from a subject;
(b) isolating histamine receptor H3 protein-encoding DNA derived from the subject;
(c) determining the nucleotide sequence of the isolated DNA; and
(d) comparing the DNA nucleotide sequence determined in step (c) with that of a control;

[19] the method of examining a disease characterized by changes in body weight or food intake of [17], wherein said method comprises the steps of:
(a) preparing a DNA sample from a subject;
(b) cleaving the prepared DNA sample with a restriction enzyme;
(c) separating the DNA fragments according to their size; and
(d) comparing the size of the detected DNA fragments with that of a control;

[20] the method of examining a disease characterized by changes in body weight or food intake of [17], wherein said method comprises the steps of:
(a) preparing a DNA sample from a subject;
(b) amplifying DNA encoding subject-derived histamine receptor H3 protein;
(c) cleaving the amplified DNA with a restriction enzyme;
(d) separating the DNA fragments according to their size; and
(e) comparing the size of the detected DNA fragment with that of a control;

[21] the method of examining a disease characterized by changes in body weight or food intake of [17], wherein said method comprises the steps of:
(a) preparing a DNA sample from a subject;
(b) amplifying DNA encoding a subject-derived histamine receptor H3 protein;
(c) dissociating the amplified DNA into single stranded DNAs;
(d) separating the dissociated single stranded DNAs on a non-denaturing gel; and
(e) comparing the mobility of the separated single stranded DNAs on the gel with that of a control;

[22] the method of examining a disease characterized by changes in body weight or food intake of [17], wherein said method comprises the steps of:
(a) preparing a DNA sample from a subject;
(b) amplifying DNA encoding a subject-derived histamine receptor H3 protein;
(c) separating the amplified DNA on a gel with gradually increasing concentration of a DNA denaturing agent; and
(d) comparing the mobility of the separated DNA on the gel with that of a control;

[23] the method of examining a disease characterized by changes in body weight or food intake of [17], wherein said method comprises the steps of:
(a) preparing a DNA sample from a subject;
(b) amplifying DNA encoding a subject-derived histamine receptor H3 protein;
(c) separating the amplified DNA with a mass spectrometer; and
(d) comparing the mass of the separated DNA with that of a control;

[24] a method of examining a disease characterized by changes in body weight or food intake, wherein the method comprises the step of detecting the expression level of the histamine receptor H3 gene, or the molecular weight of the expressed gene;

[25] the method of examining a disease characterized by changes in body weight or food intake of [24], wherein said method comprises the steps of:
(a) preparing an RNA sample from a subject;
(b) detecting the amount or molecular weight of an RNA encoding the histamine receptor H3 protein contained within the RNA sample; and
(c) comparing the detected amount or molecular weight of the RNA encoding the histamine receptor H3 protein with that of a control;

[26] the method of examining a disease characterized by changes in body weight or food intake of [24], wherein said method comprises the steps of:
(a) preparing a protein sample from a subject;
(b) detecting the amount or molecular weight of the histamine receptor H3 protein contained within the protein sample; and
(c) comparing the detected amount or molecular weight of the histamine receptor H3 protein with that of a control;

[27] an agent for examining a disease characterized by changes in body weight or food intake, wherein said agent comprises an oligonucleotide that is at least 15 nucleotides long and hybridizes to the histamine receptor H3 gene or the regulatory region of this gene;

[28] an agent for examining a disease characterized by changes in body weight or food intake, wherein said agent comprises an antibody that binds to the histamine receptor H3 protein;

The present inventors found that aberrations of the histamine receptor H3 genes (GenBank accession Nos. AB045369 and AB419000) are related to diseases exhibiting changes in body weight or food intake and such. Therefore, DNA encoding normal histamine receptor H3 protein, and the histamine receptor H3 protein itself, are considered useful for treatment and prevention of diseases exhibiting changes in body weight or food intake and such. Changes in body weight or food intake according to this invention refer to an increase or decrease in body weight or food intake.

The present inventors found that histamine receptor H3 gene knockout mice exhibited increased body weight and food intake. Therefore, histamine receptor H3 protein-encoding DNA, the histamine receptor H3 protein, and its agonists usually lead to a decrease in body weight and food intake. Its antagonists may comprise the effect of increasing body weight or food intake. However, in functions important to an organism, such as appetite, compensating functions may cause exhibition of an effect opposite to normal (Donald J. M. et al., Nature Medicine 4: 718-721, 1998; Thierry P. et al., Nature Medicine 4: 722-726, 1998). Thus when compensating functions operate, it is possible that histamine receptor H3 protein-encoding DNA, the histamine receptor H3 protein, and its agonists can comprise the reverse effect of increasing body weight or food intake, and that its antagonists can comprise the effect of decreasing body weight or food intake. Furthermore, histamine receptor H3 protein agonists or antagonists may comprise the function of decreasing body weight or food intake, or conversely, comprise the function of increasing body weight or food intake, depending on their type.

Therefore, histamine receptor H3 protein-encoding DNA, the histamine receptor H3 protein, its agonists and antagonists may become pharmaceutical agents for treatment or prevention of diseases characterized by changes (increases or decreases) in body weight or food intake.

The present invention provides pharmaceutical agents for treatment or prevention of diseases characterized by changes in body weight or food intake, in which the active ingredient is comprised by DNA encoding the histamine receptor H3 protein, or by the histamine receptor H3 protein.

Specific examples of "diseases characterized by changes in body weight or food intake" as used herein include bulimia, anorexia, or obesity, but there are no particular limitations as long as they are diseases which exhibit changes in body weight or food intake. "Histamine receptor H3 protein-encoding DNA" in the pharmaceutical agent of the present invention may be chromosomal DNA or cDNA. Chromosomal DNA encoding the histamine receptor H3 protein can be obtained, for example, by preparing a chromosomal DNA library from cells and such, and then screening the library using a probe that hybridizes to the histamine receptor H3 protein-encoding DNA. Furthermore, histamine receptor H3 protein-encoding DNA can be obtained by extracting an RNA sample from tissues such as the brain, which is considered to express the histamine receptor H3 protein, and then applying gene amplification techniques such as RT-PCR using a primer that hybridizes to the histamine receptor H3 protein-encoding DNA.

"Histamine receptor H3 protein" in the pharmaceutical agent of this invention can be obtained as a natural protein, and also prepared as a recombinant protein using transgenic techniques. The natural protein can be prepared, for example, by a method using affinity chromatography using antibodies against the histamine receptor H3 protein on a tissue extract, such as that of the brain, where the histamine receptor H3 protein is considered to be expressed. The recombinant protein can be prepared by culturing cells transformed with histamine receptor H3 protein-encoding DNA.

There are no particular limitations as to the animals from which "histamine receptor H3 protein-encoding DNA" and "histamine receptor H3 protein" in the pharmaceutical agent of this invention can be derived. When used for treatment or prevention of human diseases, they are preferably derived from mammals (for example, humans, monkeys, mice, rats, cows, pigs, and dogs), and most preferably from humans.

The "histamine receptor H3 protein-encoding DNA" and "histamine receptor H3 protein" may be mutants whose nucleotide sequences and amino acid sequences have been modified, so long as they comprise therapeutic or preventive effects toward diseases characterized by changes in body weight or food intake. Such mutants may be natural or artificial. Methods for preparing mutants artificially are well known to those skilled in the art. For example, the following methods are known: the Kunkel's method (Kunkel, T. A. et al., Methods Enzymol. 154, 367-382 (1987)); the double-primer method (Zoller, M. J. and Smith, M., Methods Enzymol. 154, 329-350 (1987)); cassette mutagenesis (Wells, et al., Gene 34, 315-23 (1985)); and the mega-primer method (Sarkar, G. and Sommer, S. S., Biotechniques 8, 404-407 (1990)).

Since the present inventors found that aberrations in the histamine receptor H3 gene are related to diseases exhibiting changes in body weight or food intake, agonists and antagonists of the histamine receptor H3 protein are expected to be utilized as drugs for treatment or prevention of diseases characterized by changes in body weight or food intake.

Other embodiments of the pharmaceutical agents of this invention relate to pharmaceutical agents used for diseases characterized by changes in body weight or food intake, comprising an agonist or antagonist of the histamine receptor H3 protein as the active ingredient.

Agonists and antagonists of the present invention may be natural compounds or artificial compounds. Known compounds may be used as the agonists and antagonists of the present invention. Furthermore, compounds isolated by the screening described below may be used. Known agonists and antagonists of the histamine receptor H3 protein include N-á-methylhistamine (Arrang J. M. et al., Nature 102: 832-, 1983), R-á-methylhistamine (Arrang J. M. et al., Nature 327: 117-, 1987), BP2.94 (Krause M. et al., J. Med. Chem. 38: 4070, 1995), SCH50971 (Hey J. A. et al., Arzneim-Forsch 48: 881-, 1998), SCH49648 (Shih N. Y. et al., J. Med. Chem. 38: 1593-, 1995), Imitet (Kathmann M. et al., Naunyn-schmiedebergs archives pharmacology 348: 498-, 1993), Immepip (Volliga R. C. et al., J. Med. Chem. 37: 332-, 1994), GT2104 (Pharmaprojects), and GT5140 (Adis R&D Insight).

Well-known histamine receptor H3 protein antagonists include Clobenpropit (Van der Goot H. et al., J. Med. Chem. 27: 511-, 1992), Ciproxifan (Ligneau X. et al., Journal of Pharmacology & Experimental Therapeutics 287: 658-, 1998), BP2.421, BP3.359, BP3.181, AQ-0145 (Murakami K. et al., Methods and findings in experimental and clinical pharmacology 17 Suppl C 70-73, 1995), UCL1390, UCL1409, UCL1199 (Ganellin C. R. et al., J. Med. Chem. 38: 3342, 1995), SCH-49648 (Sippl W. et al., Quant. Struct.-Act. Relat. 14: 121-, 1995), Pharmaprojects No. 4584, Pharmaprojects No. 4841, 4-(3-(4-Ethynylphenoxy)propyl)-1H-imidazole maleate, and GR-175737 (Clitherow J. W. et al., 10th Camerino-Noowijkerhout Symposium On Perspectives In Receptor Research, Noordwijkerhout, The Netherland: 1995).

When using the histamine receptor H3 protein-encoding DNA of this invention, the histamine receptor H3 protein, the agonists or the antagonists of this protein, or the below-mentioned compounds obtained by the screening of this invention as pharmaceutical agents for treatment or prevention of diseases characterized by changes in body weight or food intake, these molecules themselves may be administered to the target animal, or they may be formulated by conventional preparation methods and then administered. Examples of oral administration include, but are not limited to, tablets, powders, capsules, suspensions, and such. Examples of transdermal administration include, but are not limited to, cataplasms and such. There are no particular limitations as to the method of administration as long as therapeutic and/or preventive effects are indicated. Thus oral administration, transdermal administration, blood administration by injection, and such may be considered. For in vivo administration of DNA encoding histamine receptor H3 protein, viral vectors including retroviruses, adenoviruses, and Sendai viruses, and non-viral vectors including liposomes, may be used. Methods of administration include in vivo and ex vivo methods.

The present invention also provides methods of screening for drug candidate compounds for treatment or prevention of diseases characterized by changes in body weight or food intake.

One embodiment thereof is a method where binding between the histamine receptor H3 protein and a candidate compound is used as an index. In this method, the candidate compound is first contacted with the histamine receptor H3 protein. Depending on the index used to detect binding with the test compound, the histamine receptor H3 protein may be in the form of, for example, a purified histamine receptor H3 protein, a form expressed in a cell or on a cell surface, a cell membrane fraction of such a cell, or a form bound to an affinity column. Test compounds used in this method may be appropriately labeled as necessary. Examples of labels include radiolabels and fluorescent labels.

In the present method, binding between the histamine receptor H3 protein and the test compounds is next detected. Binding between the histamine receptor H3 protein and the test compound can be detected, for example, using a label attached to a test compound that binds to the histamine receptor H3 protein. When a test compound binds to histamine receptor H3 protein expressed on a cell surface, the intracellular signal transduction caused (for example, histamine receptor H3 activation, phospholipase C activation, change in $Ca^{2+}$ or cATP concentration, and change in pH) can also be used as an index for detection.

In the present method, a test compound that binds to the histamine receptor H3 protein is then selected. According to this method, compounds isolated as compounds that bind to histamine receptor H3 protein include agonists and antagonists. To evaluate whether the isolated compound is an agonist, one can, for example, contact a test compound with histamine receptor H3 protein expressed on a cell surface, and then determine whether intracellular signal transduction indicating protein activation takes place. Compounds that cause such intracellular signal transduction can be histamine receptor H3 protein agonists. To evaluate whether the isolated compound is an antagonist, one can, for example, contact a test compound in the presence of a ligand with histamine receptor H3 protein expressed on a cell surface, and then determine whether intracellular signal transduction indicating protein activation takes place. Compounds that inhibit intracellular signal transduction in response to ligand stimulation can be histamine receptor H3 protein antagonists.

Agonists and antagonists isolated by the present method become drugs for treatment or prevention of diseases such as those characterized by changes in body weight or food intake. Furthermore, agonists and antagonists are useful as compounds capable of artificially inducing diseases characterized by changes in body weight or food intake and such, and for studies on mechanism elucidation of diseases characterized by changes in body weight or food intake and such.

Another embodiment of the screening of the present invention is a method using expression of the histamine receptor H3 gene as an index. The present inventors elucidated that an aberration in the histamine receptor H3 gene relates to diseases exhibiting changes in body weight or food intake and such. Therefore, compounds that increase or decrease the expression level of normal histamine receptor H3 gene are expected to become drug candidate compounds for treatment or prevention of diseases characterized by changes in body weight or food intake.

In this method, a cell expressing the histamine receptor H3 gene is first contacted with a test compound. The "cell" used herein may be derived from humans, monkeys, mice, rats, cows, pigs, or dogs, but is not limited to these origins. As "a cell expressing the histamine receptor H3 gene", a cell expressing endogenous histamine receptor H3 gene, or a cell which expresses transferred exogenous histamine receptor H3 gene can be used. A cell expressing the exogenous histamine receptor H3 gene can generally be prepared by transfecting an expression vector, into which the histamine receptor H3 gene has been integrated, into a host cell. The expression vector can be prepared by conventional genetic engineering techniques.

There are no particular limitations as to the test compound used in this method. Examples include, but are not limited to, single compounds such as natural compounds, organic compounds, inorganic compounds, proteins, and peptides, as well as compound libraries, gene library expression products, cell extracts, cell culture supernatants, fermented microbial products, marine biological extracts, and plant extracts.

"Contact" of the test compound with the cell expressing histamine receptor H3 gene is normally performed by adding the test compound into a culture medium solution of cells expressing the histamine receptor H3 gene, but is not limited to this method. When the test compound is a protein or such, "contact" can be performed by transfecting the cell with a DNA vector expressing that protein.

In this method, histamine receptor H3 gene expression level is then measured. Herein, "gene expression" includes both transcription and translation. Measurement of gene expression level can be carried out using methods well known to those skilled in the art. For example, mRNA can be extracted from cells expressing the histamine receptor H3 gene according to standard methods, and then used as a template to measure gene transcription level using Northern hybridization or RT-PCR. Furthermore, gene translation level can be measured by recovering a protein fraction from cells expressing the histamine receptor H3 gene, and then detecting histamine receptor H3 protein expression using electrophoretic methods such as SDS-PAGE. Gene translation level can also be measured by performing Western blotting using antibodies against the histamine receptor H3 protein to detect that protein's expression. There are no particular limitations as to the antibodies used for detecting histamine receptor H3 protein as long as they are detectable antibodies. For example, monoclonal antibodies and polyclonal antibodies can both be used.

In the present method, compounds that increase or decrease expression level compared to expression level when the test compound is absent (the control) are then selected. Compounds thus selected become drug candidate compounds for treatment or prevention of diseases characterized by changes in body weight or food intake.

Another embodiment of the screening method of the present invention uses a reporter gene to identify compounds of this invention that increase or decrease the expression level of the histamine receptor H3 gene.

In the present method, a test compound is first contacted with a cell or cell extract that includes DNA comprising a structure in which a reporter gene and the transcription regulatory region of the histamine receptor H3 gene are functionally linked. Herein, the expression "functionally linked" means that a reporter gene and transcription regulatory region of the histamine receptor H3 gene are linked such that expression of the reporter gene is induced when a transcription factor binds to the transcription regulatory region of the histamine receptor H3 gene. Therefore, even if the reporter gene is linked to another gene and forms a fusion protein with the other gene product, as long as fusion protein expression is induced when a transcription factor binds to the transcription regulatory region of the histamine receptor H3 gene, it is included in the meaning of the above-mentioned expression, "functionally linked". One skilled in the art can use conventional methods, based on the cDNA nucleotide sequence of the histamine receptor H3 gene, to obtain the transcription regulatory region of the histamine receptor H3 gene existing in the genome.

There are no particular limitations as to the reporter gene used in the present method as long as its expression is detectable. Examples of such genes include the CAT gene, lacZ gene, luciferase gene, and GFP gene. An example of "cells that include DNA comprising a structure in which a reporter gene and the transcription regulatory region of the histamine receptor H3 gene are functionally linked" includes cells transfected with a vector in which such a structure has been inserted. Such a vector can be prepared by methods well known to those skilled in the art. Transfer of vectors into cells can be performed by conventional methods such as calcium phosphate precipitation, pulse electroporation, lipofectamine method, and microinjection method. "Cells that include DNA comprising a structure in which a reporter gene and the transcription regulatory region of the histamine receptor H3 gene are functionally linked" also include cells in which the structure is inserted into the chromosome. Insertion of a DNA structure into a chromosome can be performed by methods conventionally used by those skilled in the art, such as gene transfer methods using homologous recombination. "Cell extracts that include DNA comprising a structure in which a reporter gene and the transcription regulatory region of the histamine receptor H3 gene are functionally linked" include, for example, cell extracts contained in a commercially available in vitro transcription translation kit to which has been added DNA comprising a structure in which a reporter gene and the transcription regulatory region of the histamine receptor H3 gene are functionally linked.

In the present method, "contact" can be performed by adding a test compound to a culture medium solution of "cells which include DNA comprising a structure in which a reporter gene and the transcription regulatory region of the histamine receptor H3 gene are functionally linked", or by adding a test compound to the above-mentioned commercially available cell extract containing such DNA. When the test compound is a protein, contact can be achieved, for example, by transfecting a DNA vector expressing that protein into the cell.

Next, in the present method, reporter gene expression level is measured. Reporter gene expression level can be measured by methods well known to those skilled in the art, and depending on the type of reporter gene. For example, if the reporter gene is the CAT gene, reporter gene expression level can be measured by detecting acetylation of chloramphenicol by the gene product. If the reporter gene is the lacZ gene, expression level can be measured by detecting the color of a pigmented compound resulting from the catalytic action of the gene expression product. If the reporter gene is the luciferase gene, expression level can be measured by detecting the fluorescence of a fluorescent compound resulting from the catalytic action of the gene expression product. If the reporter gene is the GFP gene, expression level can be measured by detecting the fluorescence of the GFP protein.

Next, in this method, compounds are selected that increase or decrease the measured reporter gene expression level compared to that measured in the absence of test compounds. Compounds thus selected will become drug candidate compounds for treatment or prevention of diseases characterized by changes in body weight or food intake.

Another embodiment of the screening method of this invention relates to methods of utilizing genetically modified nonhuman higher animals whose expression of the histamine receptor H3 gene is artificially inhibited.

The present inventors found a relationship between aberration of the histamine receptor H3 gene and diseases exhibiting increase in body weight or food intake and such, by analyzing genetically modified nonhuman higher animals whose expression of the histamine receptor H3 gene was artificially inhibited. Therefore, the present invention provides genetically modified nonhuman higher animals in which histamine receptor H3 gene expression is artificially inhibited, where such animals are useful as animal models for diseases exhibiting an increase in body weight or food intake and such. Such genetically modified nonhuman higher animals can be used for screening pharmaceutical agents for treatment or prevention of these diseases.

In the screening methods of the present invention that use this kind of genetically modified nonhuman higher animals, a test compound is first administered to the nonhuman higher animal whose expression of the histamine receptor H3 gene is artificially inhibited.

In the present method, the expression "gene expression is artificially inhibited" includes both complete and partial inhibition. Furthermore, it includes cases where expression of one of the gene pair is inhibited. Inhibition may be carried out using methods conventionally known to those skilled in the art. Examples include methods using genetic modification techniques (including conditional genetic modification techniques due to introduction of enzymes that promote recombination of target gene sites such as Cre in Cre-lox) methods using antisense DNA, or methods using RNAi techniques.

"Nonhuman higher animal" according to this method refers to invertebrates and vertebrates excluding humans. Examples of nonhuman higher animals in which expression of genes can be artificially inhibited where genetic modification techniques have been applied can include nonhuman mammals and insects, but are more preferably nonhuman mammals (for example, rodents such as mice and rats).

Preparation of animals whose genes have been modified can be carried out, for example, as follows. First, a DNA fragment containing a target gene is cloned, and based on this, a homologous recombinant vector for endogenous target gene modification is constructed. The vector for homologous recombination comprises 1) a target gene nucleotide sequence or its expression regulatory region, in which at least one part is deleted and/or mutated, 2) a target gene nucleotide sequence or its expression regulatory region, in which nucleotides and polynucleotides have been inserted, and/or 3) a target gene nucleotide sequence or its expression regulatory region, in which other genes have been inserted. There are no limitations as to the site of the aforementioned deletion/mutation and/or insertion, as long as the nucleotide sequence causes loss of target gene activity.

Examples of genes to be inserted include neomycin resistant, thymidine kinase, and diphtheria toxin genes. Combinations of such genes can also be considered. There are no particular limitations as to the basic framework of the vector for homologous recombination, and pKONeo (lexicon) and such may be used.

Genetically modified nonhuman mammalian cells are prepared by 1) introducing a constructed vector for homologous recombination into a nonhuman mammalian cell capable of differentiating into an individual (for example, embryonic stem cells (ES cells)), and 2) performing homologous recombination with the endogenous target gene. Cells in which expression of both genes of the gene pair is inhibited can be prepared by, for example, methods for selecting cells with high concentrations of neomycin. Introduction of the vector for homologous recombination into cells can be performed by methods well known to those skilled in the art. A more specific example is electroporation.

In the present method, when ES cells are used as the animal cells capable of differentiating into an individual, chimeric embryos can be prepared, for example, by injecting the cells into blastocysts, implanting the embryos into the uteri of pseudopregnant animals, and then obtaining litters. To allow sorting of chimeric animals comprising tissues derived from genetically modified ES cells, blastocysts are preferably selected such that external characteristics of the prepared individual (for example, coat color) will differ between those comprising tissues derived from genetically modified ES cells, and those comprising tissues derived from blastocysts. Furthermore, whether or not a chimeric animal comprises reproductive tissues derived from genetically modified ES cells can be conventionally determined by observing the coat color of offspring, which were obtained by crossing that chimeric nonhuman mammal with an appropriate line of nonhuman mammal of the same species. Other methods that may also be used include performing a PCR reaction using DNA extracted from reproductive cells of the chimeric nonhuman mammalian animal as a template, and then detecting the presence of the inserted gene.

Whether an animal obtained by crossing the chimeric animal with an appropriate line of the same animal species is a genetically modified heterozygous animal can be determined, for example, using PCR and Southern hybridization using DNA extracted from the animal's cells as a template. Furthermore, genetically modified homozygous animals can be produced by crossing genetically modified heterozygous animals with each other. The above-mentioned determination method can be used to determine whether or not offspring obtained by crossing are genetically modified homozygous animals.

Production of genetically modified animals is not limited to the above-described methods. For example, genetically modified animals can be produced by following techniques for cloning animals using somatic cells. More specifically, somatic cells other than ES cells (for example, dermal cells) can be used to produce genetically modified animal cells by following methods similar to those in the case of ES cells. Furthermore, genetically modified animals can be produced from these genetically modified animal cells by applying techniques for producing somatic cell clones.

A test compound can be administered to genetically modified nonhuman higher animals thus prepared, for example and without limitation, by oral administration or injection. When the test compound is a protein, for example, a viral vector comprising a gene encoding that protein can be constructed, and its infectivity can be used to transfer the gene into the nonhuman higher animals.

The next step in this method is to measure any one of body weight, food intake, blood insulin level, or blood leptin level in the nonhuman higher animals.

The method for measuring the body weight, food intake, blood insulin level, or blood leptin level of the nonhuman higher animal in the present method is described using mice as an example. Body weight is measured on an animal balance. Food intake is measured as the difference in the feed weight before and after food intake. Blood insulin level and blood leptin level can be measured by EIA sandwich method using a microplate (MORINAGA). To measure blood insulin level, heparinized blood drawn from a vein is centrifuged to obtain plasma components. Plasma and guinea pig anti-insulin serum are reacted on an antibody solid-phase plate. After washing the plate with a buffer, anti-guinea pig enzyme labeled antibody is added and reacted. The plate is again washed with buffer, and an enzyme substrate solution (o-phenylediamine) is added and reacted. The reaction is quenched with 1N sulfuric acid, and absorbance is measured. A standard curve is drawn using the absorbance of an insulin standard curve solution, and the insulin level in the plasma is measured. To measure blood leptin level, the obtained blood plasma and guinea pig anti-mouse leptin serum are reacted on an antibody solid-phase plate. After washing the plate, the enzyme labeled guinea pig IgG antibody solution is added and reacted. The plate is washed again, and an enzyme substrate solution (TMB; 3,3',5,5'-tetramethylbentidine) is added and reacted. After quenching the reaction with 1N sulfuric acid, absorbance is measured. A standard curve is drawn using the absorbance of a leptin standard curve solution, and the leptin level in the plasma is measured.

The next step in this method is to select test compounds that increase or decrease any one of body weight, food intake, blood insulin level, or blood leptin level, as compared to in the absence of test compounds. Compounds thus selected are drug candidate compounds for treatment or prevention of diseases characterized by changes in body weight or food intake.

Cells prepared from nonhuman higher animals that can artificially inhibit histamine receptor H3 gene expression are useful cells for screening and such of drug candidate compounds used for treatment or prevention of diseases exhibiting changes in body weight or food intake. For example, cells can be transfected with a gene library, and genes that respond to histamine receptor H3 protein ligands (by increasing or decreasing intracellular signal transduction in these cells) can be cloned such that proteins encoded by these genes can substitute the function of the histamine receptor H3 protein. Examples of cells that can be used in such screening include, but are not limited to, primary cultured cells and established cells.

The present invention provides methods for examining diseases characterized by changes in body weight or food intake. In the present example, histamine receptor H3 gene knockout mice displayed the characteristics of increased body weight or food intake. This suggests that diseases characterized by changes in body weight or food intake are caused by histamine receptor H3 gene mutations or expression aberrations. Therefore, examination of diseases characterized by changes in body weight or food intake can be performed by analyzing mutations and expression aberrations in the histamine receptor H3 gene.

In the present method, "examination of diseases characterized by changes in body weight or food intake" includes 1) examination of subjects exhibiting symptoms of diseases characterized by changes in body weight or food intake due to a mutation in the histamine receptor H3 gene, and 2) examination of mutations of the histamine receptor H3 gene performed to determine whether the subject is prone to diseases characterized by changes in body weight or food intake due to a mutation in histamine receptor H3 gene. For example, even if symptoms are not yet apparent, a mutation in one of the histamine receptor H3 alleles is thought to lead to a greatly increased risk of being affected by diseases characterized by changes in body weight or food intake. Examinations for identifying a subject comprising a mutation in one of the histamine receptor H3 alleles (a carrier) are also included in the methods of examination of this invention.

One embodiment of the methods of examination of this invention is a method for directly determining the nucleotide sequence of a subject's histamine receptor H3 gene. In this method, a DNA sample is first prepared from the subject. For example, the DNA sample can be prepared based on chromosomal DNA or RNA extracted from cells or tissues from the subject's brain or the like. The DNA sample of this method can also be prepared from chromosomal DNA by, for example, cleaving the chromosomal DNA with an appropriate restriction enzyme, cloning these fragments into a vector, and then preparing a genomic library. The DNA sample of this method can be prepared from RNA, for example, by preparing a cDNA library from RNA using reverse transcriptase.

The next step of the present method is to select DNAs encoding a subject-derived histamine receptor H3 protein. Herein, "select" means to specifically isolate a histamine receptor H3 protein-encoding DNA (a part or whole of the histamine receptor H3 gene of the subject, or the regulatory region of that gene). Selection of histamine receptor H3 protein-encoding DNA can be performed by screening genomic libraries and cDNA libraries using a probe that hybridizes to histamine receptor H3 protein-encoding DNA. DNAs encoding the histamine receptor H3 protein can also be selected by PCR using a primer that hybridizes to histamine receptor H3 protein-encoding DNA, and using a genomic DNA library, cDNA library, or RNA as a template.

The next step in the present method is to determine the nucleotide sequence of the selected DNA. The nucleotide sequence of the selected DNA can be determined using methods well known to those skilled in the art.

Next, in the present method, the determined DNA nucleotide sequence is compared with a control. The control of this method refers to the sequence of a normal (wild type) histamine receptor H3 gene or the regulatory region of this gene. Generally, since the histamine receptor H3 gene sequence of a healthy individual, or the regulatory region of this gene, is considered to be normal, the phrase, "compared with a control" in the above-mentioned step usually refers to comparison with the sequence of a healthy individual's histamine receptor H3 gene, or the regulatory region of this gene. However, this comparison can also be made with sequences for a wild-type histamine receptor H3 gene, or regulatory region thereof, as registered in GenBank and such. A subject is suspected to have a disease characterized by changes in body weight or food intake if such a comparison reveals a difference between the subject's histamine receptor H3 gene, or regulatory region thereof, and the control.

The methods of examination of this invention encompass various methods as well as the above-mentioned method that determines the nucleotide sequence of DNA directly derived from a subject.

In one embodiment of such methods, a DNA sample is first prepared from a subject. The DNA sample is then cleaved with a restriction enzyme, the DNA fragments are separated according to size, and the sizes of these DNA fragments are compared to a control. In another embodiment, a DNA sample is first prepared from a subject, and using DNA as a primer, DNA encoding the subject-derived histamine receptor H3 protein is amplified. This amplified DNA is then cleaved with a restriction enzyme, DNA fragments are separated according to size, and the sizes of the detected DNA fragments are compared to a control.

The above method may, for example, utilize Restriction Fragment Length Polymorphism/RFLP, PCR-RFLP method, and the like. When a mutation exists at a restriction enzyme recognition site, or when nucleotide insertion(s) or deletion(s) exist in a DNA fragment generated by restriction enzyme treatment, the size of the fragments generated by that restriction enzyme treatment will differ from the size of the controls. A portion containing a mutation is amplified by PCR, and then treated with several restriction enzymes to detect the mutation/s using differences in band mobility revealed after electrophoresis. Alternatively, the existence of a mutation on the chromosomal DNA can be detected by treating the chromosomal DNA with restriction enzymes, subjecting the DNA fragments to electrophoresis, and then carrying out Southern blotting using a probe DNA of the present invention. The restriction enzymes to be used can be appropriately selected in accordance with respective mutations. Southern blotting can be conducted not only on genomic DNA but also on cDNAs directly digested with restriction enzymes, where the cDNAs are synthesized from RNAs prepared from subjects using reverse transcriptase. Alternatively, after amplifying a part or whole of the histamine receptor H3 gene by PCR using cDNA as a template, the cDNAs can be digested with restriction enzymes, and differences in mobility can be examined.

In one embodiment of the method of examination of the present invention, a DNA sample is first prepared from a subject. Next, subject-derived DNAs encoding histamine receptor H3 protein are amplified using DNA as the primer. The amplified DNA is dissociated into single stranded DNAs, the dissociated single stranded DNAs are separated on a non-denaturing gel, and the mobility of the separated single stranded DNAs on this gel is compared with the mobility of a control.

The above method may, for example, utilize the PCR-SSCP (single-strand conformation polymorphism) method ("Cloning and polymerase chain reaction-single-strand conformation polymorphism analysis of anonymous Alu repeats on chromosome 11." Genomics 1992, Jan. 1, 12(1): 139-146; "Detection of p53 gene mutations in human brain tumors by single-strand conformation polymorphism analysis of polymerase chain reaction products." Oncogene 1991, Aug. 1; 6(8): 1313-1318; "Multiple fluorescence-based PCR-SSCP analysis with postlabeling." PCR Methods Appl. 1995, Apr.

1; 4(5): 275-282). This method is particularly preferable for screening large numbers of DNA samples since it is comparative simple to operate and requires only a small amount of test sample. The principle of this method is as follows. A double stranded DNA is dissociated to form a single-stranded DNA fragment, and each strand forms a unique higher conformation that depends on its nucleotide sequence. DNAs thus dissociated are subject to electrophoresis on a non-denaturing polyacrylamide gel, where complementary single-stranded DNAs of equal chain length move to different positions according to differences in their respective higher conformations. The substitution of even a single base results in a change in single-stranded DNA conformation, thus resulting in a difference in mobility during polyacrylamide gel electrophoresis. Accordingly, the presence of a DNA fragment mutation, such as a single point mutation, deletion, or insertion, can be detected by detecting these changes in mobility.

More specifically, a part or whole of the histamine receptor H3 gene is first amplified by PCR or the like. Preferably, a region of about 200 to 400 bp in length is amplified. The region to be amplified includes all exons and all introns of the histamine receptor H3 gene, as well as its promoters and enhancers. PCR can be conducted under appropriate reaction conditions selected by those skilled in the art. The amplified DNA products can be labeled using primers labeled with isotopes such as $^{32}P$, fluorescent dyes, biotin, or the like. Alternatively, the amplified DNA products can also be labeled by carrying out PCR in which the PCR reaction solution includes substrate nucleotides labeled with isotopes such as $^{32}P$, fluorescent dyes, biotin, and so on. Furthermore, labeling can also be carried out by adding the amplified DNA fragments to substrate nucleotides labeled with isotopes such as $^{32}P$, fluorescent dyes, biotin, and so on, using the Klenow enzyme or the like. Labeled DNA fragments thus-obtained are denatured by heating and the like, and then subjected to electrophoresis on a polyacrylamide gel without a denaturant such as urea. The separation conditions for the DNA fragments can be improved by adding appropriate amounts (about 5% to 10%) of glycerol to the polyacrylamide gel. Although electrophoresis conditions vary depending on the characteristics of respective DNA fragments, it is usually carried out at room temperature (20° C. to 25° C.). If this does not achieve preferable separation, a temperature between 4° C. to 30° C. can be selected to facilitate optimum mobility. After electrophoresis, DNA fragment mobility is detected using a scanner for detecting fluorescence, autoradiography with X-ray films, or the like, and results are then analyzed. When a band with different mobility is detected, the presence of a mutation can be confirmed by directly excising the band from the gel, amplifying it again using PCR, and directly sequencing the amplified fragment. Further, when not using labeled DNAs, the bands can be also detected by staining the gel after electrophoresis with ethidium bromide, silver, and such.

In another embodiment of the examination method of the present invention, a DNA sample is first prepared from a subject. Next, subject-derived DNAs encoding the histamine receptor H3 protein are amplified using DNA as a primer. The amplified DNAs are separated on a gel comprising a gradually increasing concentration of DNA denaturant. Mobility of the separated DNAs on this gel is compared with that of a control.

The denaturant gradient gel electrophoresis method (DGGE method) can be exemplified as one of such methods. The DGGE method is a method of separating DNA fragments according to differences in their respective instabilities, by electrophoresis of a mixture of DNA fragments through a polyacrylamide gel comprising a denaturant concentration gradient. When an unstable DNA fragment containing a mismatch reaches a certain concentration of denaturant within the gel, the instability causes the DNA sequence around the mismatch to partially dissociate to single strands. The mobility of this partially dissociated DNA fragment is thus drastically reduced. Since this mobility differs from the mobility of the complete double stranded DNA without the dissociated portion, the two can be separated. Specifically, a part or whole of the histamine receptor H3 gene is amplified by PCR and the like using a primer of the present invention and such, electrophoresed on a polyacrylamide gel with a gradient concentration of denaturant such as urea, and these results are then compared with those of a control. A mutation can be identified by detecting differences in DNA fragment mobility, since a DNA fragment with mutations will have greatly reduced mobility, due to dissociation into single-stranded DNAs in parts of the gel where denaturant concentration is relatively low.

Furthermore, in another embodiment of the present invention, examination of diseases characterized by increase in body weight or change in food intake can be performed using a mass spectrometer (MASS). A DNA sample is first prepared from a subject, subject-derived DNA encoding histamine receptor H3 protein is then amplified, the amplified DNA is separated with a mass spectrometer, and the mass of the separated DNA is compared to that of the control.

In addition to the above-mentioned methods, the Allele Specific Oligonucleotide (ASO) hybridization method can be also used to detect a mutation at a specific site. Oligonucleotides comprising a nucleotide sequence in which a mutation is predicted to exist are prepared, and then hybridized with a DNA test sample. The hybridization efficiency will be reduced by the existence of a mutation. This decrease in hybridization efficiency can be detected by, for example, using Southern blotting, or methods using the quenching property of specific fluorescent reagents whose fluorescence is quenched when they intercalate into a gap in the hybrid. Furthermore, detection is also possible using the ribonuclease A mismatch truncation method. Specifically, a part or whole of the histamine receptor H3 gene is amplified using PCR or the like, and the amplified products are hybridized with labeled RNAs prepared from histamine receptor H3 cDNA and such, which is incorporated into a plasmid vector or the like. Sites where a mutation exists form single-stranded regions which can be cleaved using ribonuclease A, and then detected using autoradiography or the like. In this way, the presence of a mutation can be detected.

Another embodiment of the method of examination of this invention is a method that uses the expression level of the gene encoding the histamine receptor H3 protein, or the molecular weight of the expression product of that gene, as an index. Herein, "expression of a gene" includes transcription and translation. Therefore, "expression product" includes mRNAs and proteins.

Genes encoding the histamine receptor H3 protein at the transcriptional level are examined by initially preparing an RNA sample from a subject. Next, the amount or molecular weight of RNA that encodes the histamine receptor H3 protein, and that is contained within that RNA sample, is determined. Next, the amount or molecular weight of the detected RNA is compared with that of the control.

This kind of method includes Northern blotting using a probe that hybridizes to histamine receptor H3 protein-encoding DNA, RT-PCR using primers that hybridize to histamine receptor H3 protein-encoding DNA, and a method using DNA microarrays hybridizing to oligonucleotides.

For examination at the level of translation of the gene encoding the histamine receptor H3 protein, a protein sample is first prepared from a subject. Next, the amount or molecular weight of histamine receptor H3 protein contained in the protein sample is detected, and then the amount or molecular weight of the detected protein is compared with that of a control.

Such methods include SDS polyacrylamide electrophoresis, Western blotting, dot blotting, immunoprecipitation, enzyme linked immunosorbent assay (ELISA), and immunofluorescence methods using antibodies that bind to the histamine receptor H3 protein.

In these methods, a subject can be suspected of having a disease characterized by changes in body weight or food intake if their expression level of the gene encoding the histamine receptor H3 protein is significantly increased or decreased from that of a control, or if the molecular weight of that gene expression product is significantly different from that of a control (the control is a healthy individual).

The present invention also provides examination agents that can be used in a method for examining diseases characterized by changes in body weight or food intake.

One such embodiment is an examination reagent that comprises an oligonucleotide at least 15 nucleotides long, that hybridizes to the histamine receptor H3 gene, or to the regulatory region of this gene.

Preferably, this oligonucleotide hybridizes specifically to the nucleotide sequence of histamine receptor H3 gene, or to the regulatory region of this gene. Herein, "hybridizes specifically" means that under normal hybridization conditions, and preferably under stringent hybridization conditions, no significant cross hybridization occurs with DNA encoding other proteins (for example, the conditions according to Sambrook et al., Molecular Cloning, Cold Spring Harbor Laboratory Press, New York, USA, 2nd edition, 1989).

The oligonucleotides can be used as probes and primers for the above-mentioned methods of examination of this invention. The length of an oligonucleotide used as a primer is normally 15 bp to 100 bp, and preferably 17 bp to 30 bp. There are no particular limitations regarding the primer, as long as it can amplify at least a part of the histamine receptor H3 gene, or the regulatory region of this gene. The above-mentioned region includes exon regions, intron regions, promoter regions and enhancer regions of the histamine receptor H3 gene.

Furthermore, when using an above-mentioned oligonucleotide as a probe, the probe has no particular limitations as long as it specifically hybridizes to at least a part of the histamine receptor H3 gene, or to the regulatory region of this gene. The probe may be a synthetic oligonucleotide, and is normally at least 15 bp long. The region that the probe hybridizes to can include, for example, exon regions, intron regions, promoter regions and enhancer regions of the histamine receptor H3 gene.

The oligonucleotides of this invention can be prepared, for example, using a commercial oligonucleotide synthesizer. Probes can be prepared as double stranded DNA fragments obtained by restriction enzyme treatment and such.

Before being used as a probe, an oligonucleotide of the present invention is preferably appropriately labeled. Methods of labeling include phosphorylation of the oligonucleotide 5' end with $^{32}P$ using T4 polynucleotide kinase, and incorporation of substrate nucleotides labeled with isotopes such as $^{32}P$, fluorescent dyes, biotin, or such, using random hexamer oligonucleotides and such as primers, and a DNA polymerase such as the Klenow enzyme (for example, random priming method).

Another embodiment of the agent for examination of this invention is an agent for examination comprising antibodies that bind to the histamine receptor H3 protein. There are no particular limitations as to the antibodies, as long as they can be used for examination, and examples include polyclonal antibodies and monoclonal antibodies. The antibodies are labeled as necessary.

Antibodies that bind to histamine receptor H3 protein may be prepared by methods well known to those skilled in the art. Polyclonal antibodies can be obtained, for example, in the following manner. Natural histamine receptor H3 protein, recombinant histamine receptor H3 protein expressed in microorganisms such as E. coli as a fusion protein with GST, or partial peptides thereof are used to immunize small animals such as rabbits, and serum is obtained. To prepare the antibodies, this serum is then purified by using, for example, ammonium sulfate precipitation, protein A column chromatography, protein G column chromatography, DEAE ion exchange chromatography, or an affinity column to which the histamine receptor H3 protein and synthetic peptides are coupled. Monoclonal antibodies are produced by, for example, using histamine receptor H3 protein or a partial peptide thereof to immunize small animals such as mice, removing the spleens from such a mouse, grinding the spleen to separate cells, fusing these cells with mouse myeloma cells using reagents such as polyethylene glycol, and then selecting from among the resulting fused cells (hybridomas), clones which produce antibodies that bind to the histamine receptor H3 protein. Next, the obtained hybridomas are transplanted to the abdominal cavities of mice, and ascites are collected from these mice. Monoclonal antibodies thus obtained are purified by, for example, ammonium sulfate precipitation, protein A column chromatography, protein G column chromatography, DEAE ion exchange chromatography, or by using an affinity column to which histamine receptor H3 protein and synthetic peptides are coupled. In this way monoclonal antibodies can be prepared.

In addition to oligonucleotides and antibodies, which are active ingredients, the agent for examination of the present invention may contain, for example, sterilized water, physiological saline, vegetable oil, surfactants, lipids, solubilizing agents, buffers, protein stabilizers (BSA, gelatin, etc.), preservatives, and such as necessary.

BEST MODE FOR CARRYING OUT THE INVENTION

Hereinafter, the present invention is specifically illustrated below with reference to Examples, but is not to be construed as being limited thereto.

EXAMPLE 1

Production of Histamine Receptor H3 Gene-Modified Mice and Analysis of These Genetically Modified Mice (1) Construction of a Vector for Homologous Recombination of Mouse Histamine Receptor H3 Gene.

Mouse histamine receptor H3 genomic clones were obtained by screening a mouse 129/Sv genomic library (Stratagene) using a rat histamine receptor H3 cDNA (Lovenberg T. W. et al., Journal of Pharmacology and Experimental Therapeutics, 293: 771-778, 2000) as a probe. The total 16760-bp nucleotide sequence of one of the clones was determined using shotgun cloning methods. This nucleotide sequence is shown in SEQ ID NO: 1.

The mouse histamine receptor H3 gene comprises three exons. A vector for homologous recombination was constructed by replacing exon 1 of these exons with a PGKneo cassette. That is, Xba I-XbaI (1.9 kb), and Sma I-Xba I (6.0 kb) fragments were placed upstream and downstream of the PGKneo cassette. Exon 1 includes a part of the transmembrane domain 2.

(2) Establishment of Histamine Receptor H3 Gene-Modified Mouse ES Cells by Homologous Recombination.

Electroporation was used to transfect the vector for homologous recombination into mouse-derived ES cells (derived from the 129 line), and neomycin resistant clones were obtained by performing G418 selection. Confirmation of genetic recombination in the ES cell clones whose histamine receptor H3 gene had been deleted by homologous recombination was carried out using Southern hybridization analysis. Selection of a wildtype allele and an allele in which homologous recombination occurred was performed by detecting the polymorphism of Bam HI newly formed due to homologous recombination. The 865 bp region of the above-mentioned Xba I-Xba I fragment (left probe), and the 965 bp region of the Sma I-Xba I fragment (right probe) were used as probes for the detection.

(3) Production of Chimeric Mice Using Histamine Receptor H3 Gene-Modified ES Cells.

Histamine receptor H3 gene-deleted ES cells (derived from 129 line) were injected into blastocysts (derived from C57BL/6N). These blastocysts were transferred directly into the uterus of foster mothers on the same day, and chimeric mice were delivered.

(4) Production of First Generation (F1) Histamine Receptor H3 Gene-Modified Mice and Analysis of the Genetically Modified Mice.

Figure 1:
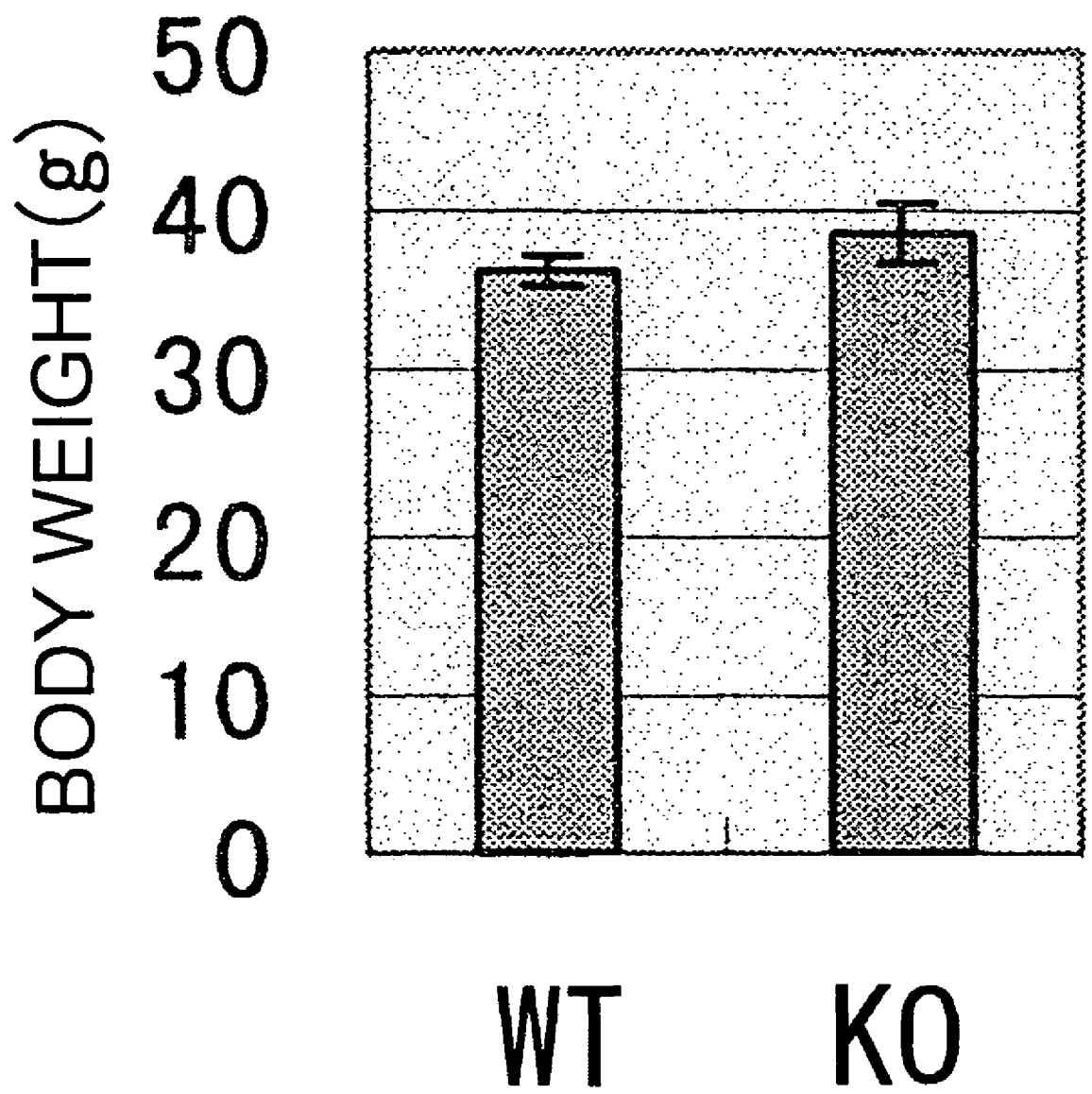
FIG. 1 shows the body weights of 20-week old wildtype mice and first generation histamine receptor H3 gene homozygous knockout mice. WT indicates wildtype mice; KO indicates histamine receptor H3 gene homozygous knockout mice (first generation).

Genetically modified heterozygous mice (F1) were produced. Genetically modified homozygous mice were obtained by intercrossing male and female genetically modified heterozygous mice. No problems were observed in the developmental process of these first generation genetically modified homozygous mice, and no significant differences in development and growth were observed when compared to wildtype littermate mice (FIG. 1).

EXAMPLE 2

Production of Second and Later Generations of Histamine Receptor H3 Gene-Modified Mice by Backcrossing, and Analysis of These Genetically Modified Mice As a consequence of the production process, genetically modified mice are produced as hybrids between the 129 line and C57BL/6 line. Therefore, important biological parameters including body weight, and behavioristic parameters cannot be examined in certain cases. In order to remove such this genetic background, which was generated in the production process of the genetically modified mice, the present inventors produced second and later generations of genetically modified mice by the method of backcrossing.

Backcrossing was performed by crossing genetically modified heterozygous male mice older than ten weeks with C57BL/6N females. From the next day after mating, the C57BL/6N females were checked for plugs. As soon as a plug was confirmed, the genetically modified heterozygous male mouse was crossed with a different C57BL/6N female. Nesting materials were provided for C57BL/6N females in which plugs were observed. Delivery was confirmed approximately 20 days later.

The babies were weaned four weeks after birth, and were divided into males and females (five animals or less per cage). Their tails were amputated at the time of weaning, and simultaneously animal identification tags were placed by ear punch. Tail amputation was carried out using surgical scissors approximately 1 cm from the end of the tail. Genomic DNA was extracted from the amputated tail, purified, and its genotype was determined using Southern analysis. Differentiation between wildtype and genetically modified heterozygous mice was performed by determining genotype.

Genetically modified heterozygous male mice were again crossed with C57BL/6N females. Mating and delivery took approximately four months per generation. Back crossing with C57BL/6N mentioned above was performed for three generations. The fourth generation genetically modified heterozygous male and female mice thus obtained were crossed to produce genetically modified homozygous mice. Mice older than ten weeks were also used for crossing genetically modified heterozygous male and female mice.

Figure 2:
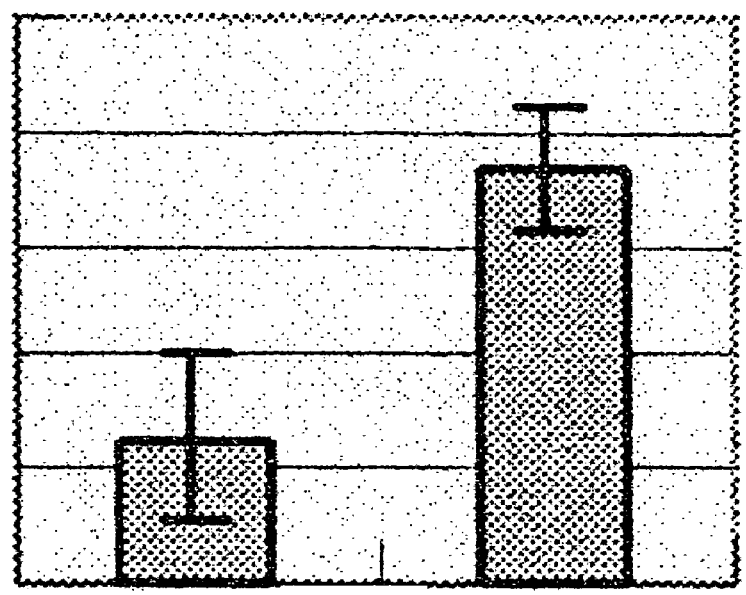
FIG. 2 shows the body weights of 20-week old wildtype mice and histamine receptor H3 gene homozygous knockout mice (fourth generation). WT indicates wildtype mice; KO indicates fourth generation histamine receptor H3 gene homozygous knockout mice.
Figure 3:
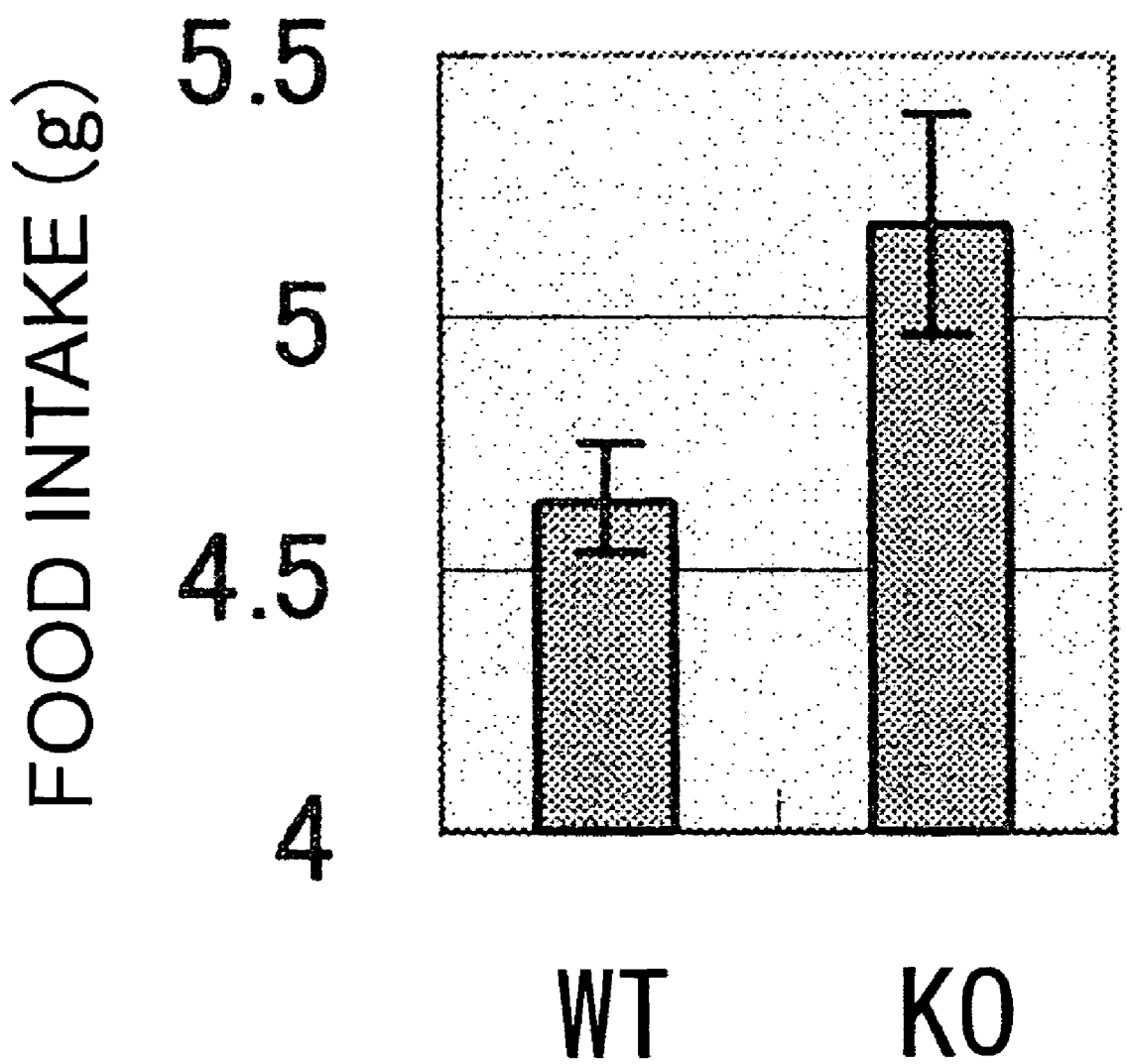
FIG. 3 shows food intake per 24 hours for wildtype mice and histamine receptor H3 gene homozygous knockout mice (fourth generation), measured over two weeks starting from 19 weeks after birth. WT indicates wildtype mice; KO indicates fourth generation histamine receptor H3 gene homozygous knockout mice.

The following was performed in a manner similar to backcrossing. The body weights of littermates obtained by crossing fourth generation genetically modified heterozygous male and female mice were determined. The results are shown in FIG. 2. Body weight was confirmed to be significantly increased in the fourth generation of genetically modified homozygous mice compared to in wildtype mice. Food intake was also measured for two weeks starting from 19 weeks after birth. Approximately 80 grams of PA-1 (ordinary diet) was set and body weight was measured the following day. This measurement was conducted daily. Results indicated that food intake was significantly increased in genetically modified homozygous mice (FIG. 3).

Figure 4:
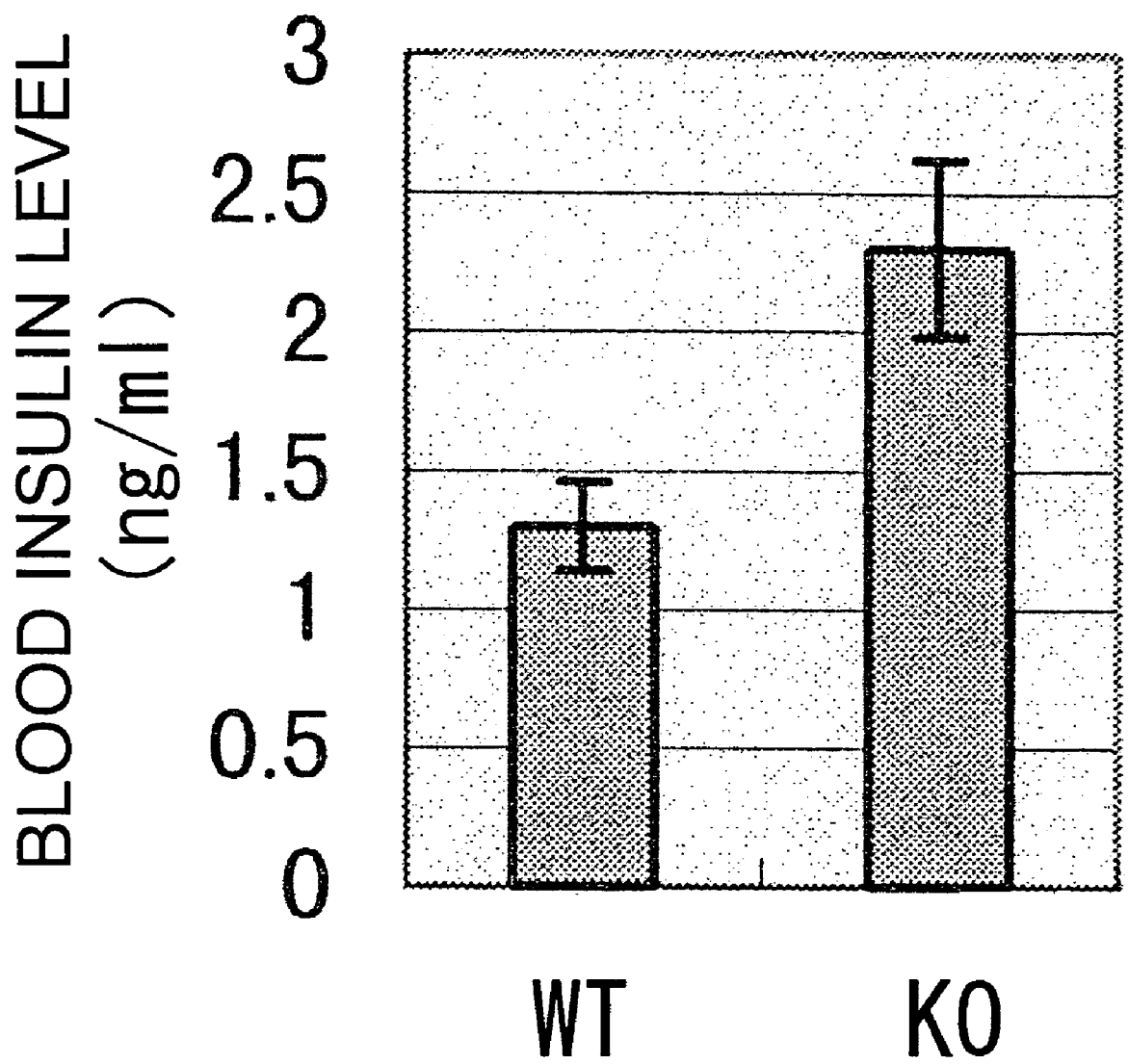
FIG. 4 shows blood insulin levels in wild type mice and in fourth generation histamine receptor H3 gene homozygous knockout mice. WT indicates wildtype mice; KO indicates fourth generation histamine receptor H3 gene homozygous knockout mice.
Figure 5:
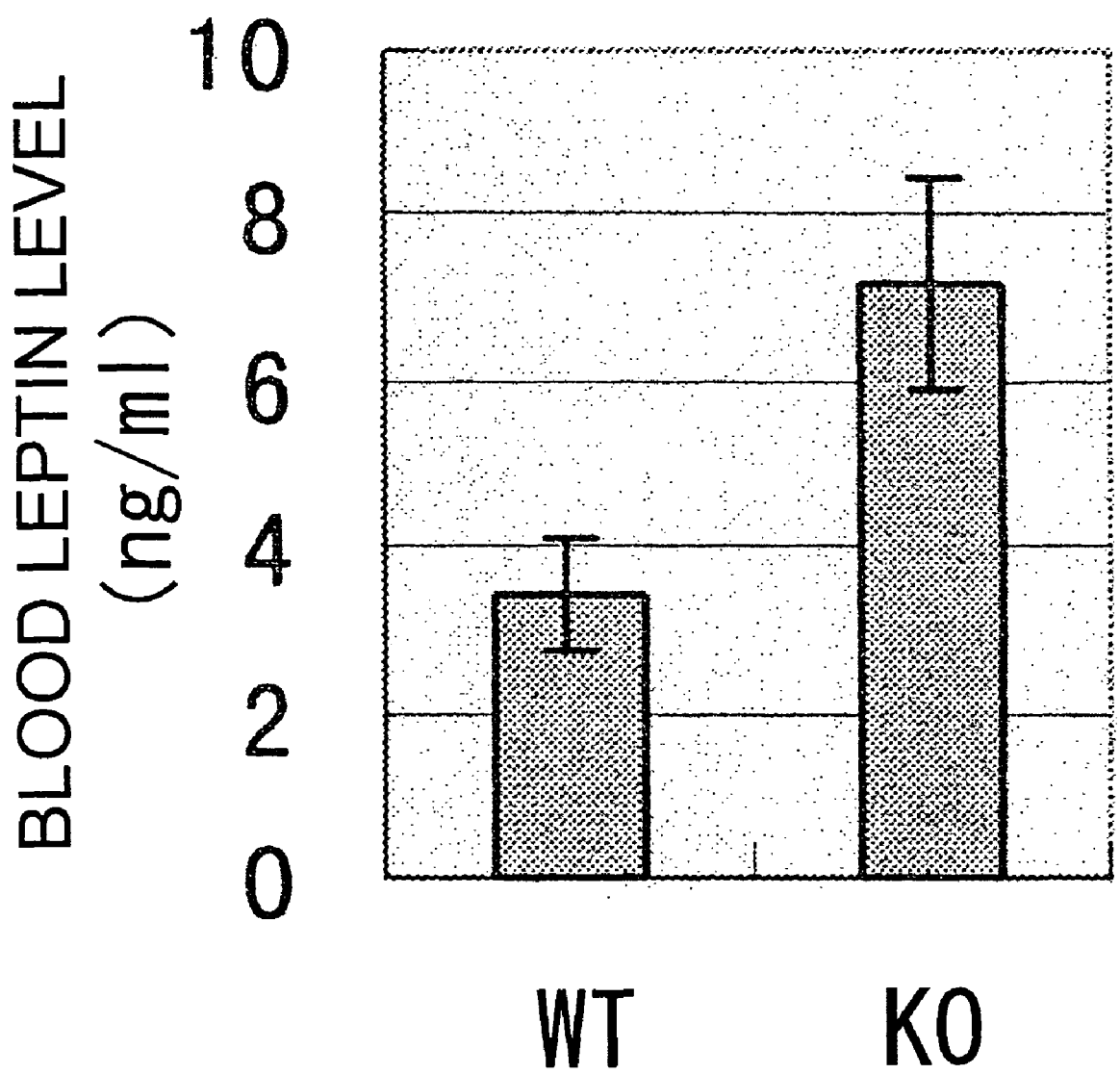
FIG. 5 shows blood leptin levels in wild type mice and in fourth generation histamine receptor H3 gene homozygous knockout mice. WT indicates wildtype mice; KO indicates fourth generation histamine receptor H3 gene homozygous knockout mice.

Furthermore, blood parameters (while feeding ad libitum) were also measured. Insulin levels and leptin levels were measured by drawing heparinized blood from the tail vein of 11 to 15 week-old mice, preparing plasma, and performing ELISA (Morinaga). These results revealed that blood insulin and leptin levels were significantly increased in genetically modified homozygous mice (FIGS. 4 and 5).

INDUSTRIAL APPLICABILITY

The present invention revealed the relationship between the histamine receptor H3 gene and changes in body weight or food intake. As a consequence, the present inventors provided methods of screening or identifying compounds that control body weight or food intake. Compounds isolated by these screening methods are expected to be compounds for the treatment of diseases characterized by changes in body weight or food intake. Furthermore, examination of these diseases has become possible by determining mutations and expression levels of the histamine receptor H3 gene.

The invention claimed is:

1. An isolated mouse cell comprising a disruption of one or both endogenous histamine receptor H3 genes, wherein said disruption results in a lack of functional histamine receptor H3 activity.

2. The cell of claim 1, wherein the cell is a cultured cell.

3. The cell of claim 1, wherein the cell is a mouse embryonic stem cell.

4. A genetically modified mouse whose genome comprises a disruption of one or both endogenous histamine receptor H3 genes, wherein a homozygous disruption results in a lack of functional histamine receptor H3 activity, and wherein a mouse homozygous for said disruption exhibits increased food intake, increased body weight, increased blood insulin level, or increased blood leptin level in comparison to a littermate control mouse.

5. The genetically modified mouse of claim 4, wherein the genetically modified mouse is homozygous for the histamine receptor H3 gene disruption.

6. The genetically modified mouse of claim 5, wherein the genetically modified mouse has increased body weight, as compared to a littermate control mouse.

7. A method of screening for a drug candidate compound for treatment or prevention of a disease characterized by changes in body weight or food intake, wherein said method comprises the steps of:

(a) administering a test compound to the genetically modified mouse of claim 5;
(b) measuring any one of body weight, food intake, blood insulin level, or blood leptin level of the genetically modified mouse; and
(c) selecting a test compound that changes the level of any one of body weight, food intake, blood insulin, or blood leptin compared to the level measured when the test compound is not administered.

8. The cell of claim 1, wherein said disruption is generated by homologous recombination.

9. The genetically modified mouse of claim 4, wherein said disruption is generated by homologous recombination.

10. The genetically modified mouse of claim 5, wherein the genetically modified mouse has increased food intake, as compared to a littermate control mouse.

11. The genetically modified mouse of claim 5, wherein the genetically modified mouse has increased blood insulin level, as compared to a littermate control mouse.

12. The genetically modified mouse of claim 5, wherein the genetically modified mouse has increased blood leptin level, as compared to a littermate control mouse.

13. The genetically modified mouse of claim 4, wherein the genetically modified mouse is heterozygous for the disruption.

* * * * *